(12) United States Patent
Siegal

(10) Patent No.: US 8,597,330 B2
(45) Date of Patent: *Dec. 3, 2013

(54) DEVICES FOR INTRODUCTION INTO A BODY VIA A SUBSTANTIALLY STRAIGHT CONDUIT TO FORM A PREDEFINED CURVED CONFIGURATION, AND METHODS EMPLOYING SUCH DEVICES

(75) Inventor: Tzony Siegal, Moshav Shoeva (IL)

(73) Assignee: NLT Spine Ltd., Kfar Saba (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/490,483

(22) Filed: Jun. 7, 2012

(65) Prior Publication Data
US 2012/0245570 A1  Sep. 27, 2012

Related U.S. Application Data

(63) Continuation of application No. 12/960,503, filed on Dec. 5, 2010, now Pat. No. 8,236,029, which is a continuation of application No. 11/813,213, filed as application No. PCT/IL2005/001393 on Dec. 28, 2005, now Pat. No. 7,918,874, and a continuation-in-part of application No. 11/028,655, filed on Jan. 5, 2005, now Pat. No. 7,503,920.

(60) Provisional application No. 60/689,570, filed on Jun. 13, 2005.

(51) Int. Cl.
A61B 17/70 (2006.01)

(52) U.S. Cl.
USPC .......................................... 606/246; 606/279

(58) Field of Classification Search
USPC ............. 606/246, 328, 79, 80, 84, 90, 92, 93, 606/96, 99, 104, 105, 86 A, 279; 623/17.11, 623/17.16
See application file for complete search history.

(56) References Cited

U.S. PATENT DOCUMENTS

| | | |
|---|---|---|
| 5,285,795 A | 2/1994 | Ryan |
| 5,702,454 A | 12/1997 | Baumgartner |
| 5,756,127 A | 5/1998 | Grisoni et al. |
| 6,387,130 B1 | 5/2002 | Stone |
| 6,599,294 B2 * | 7/2003 | Fuss et al. ...................... 606/99 |
| 7,037,339 B2 | 5/2006 | Houfburg |
| 7,267,687 B2 | 9/2007 | McGuckin, Jr. |
| 7,547,319 B2 | 6/2009 | Segal |
| 7,785,368 B2 | 8/2010 | Schaller |
| 7,905,920 B2 | 3/2011 | Galea |
| 7,909,872 B2 | 3/2011 | Zipnick |
| 7,918,874 B2 | 4/2011 | Siegal |

(Continued)

Primary Examiner — Pedro Philogene
Assistant Examiner — David Comstock
(74) Attorney, Agent, or Firm — Mark M. Friedman

(57) ABSTRACT

A device for introduction into a body in a straight configuration and assuming within the body a predefined curved configuration, includes an elongated element formed from a number of segments interconnected so as to form effective hinges therebetween. When the elongated element is confined to a straight state, the effective hinges transfer compressive forces from each segment to the next so that the elongated element can be pushed to advance it through a conduit. When the elongated element is not confined to a straight state, the effective hinges allow deflection of each segment relative to adjacent segments until abutment surfaces of the segments come into abutment, thereby defining a fully flexed state of the elongated element with a predefined curved configuration. The device can be produced with a wide range of two-dimensional and three-dimensional curved forms, and has both medical and non-medical applications.

7 Claims, 20 Drawing Sheets

(56) References Cited

U.S. PATENT DOCUMENTS

| | | |
|---|---|---|
| 7,938,860 B2 | 5/2011 | Trieu |
| 2001/0032017 A1 | 10/2001 | Alfaro et al. |
| 2005/0278023 A1 | 12/2005 | Zwirkoski |
| 2008/0300601 A1 | 12/2008 | Fabian et al. |
| 2008/0312743 A1 | 12/2008 | Vila et al. |
| 2009/0270873 A1 | 10/2009 | Fabian |
| 2010/0185290 A1 | 7/2010 | Compton |
| 2011/0009969 A1 | 1/2011 | Puno |

\* cited by examiner

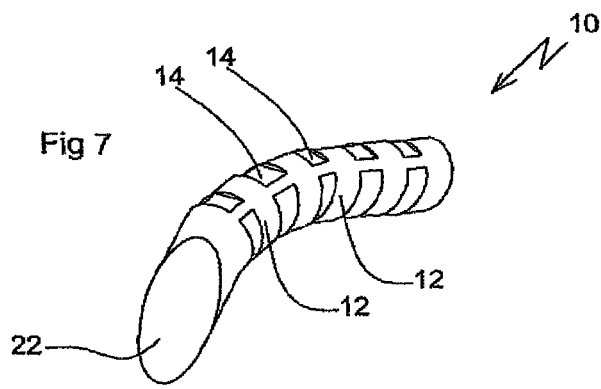
Fig 7
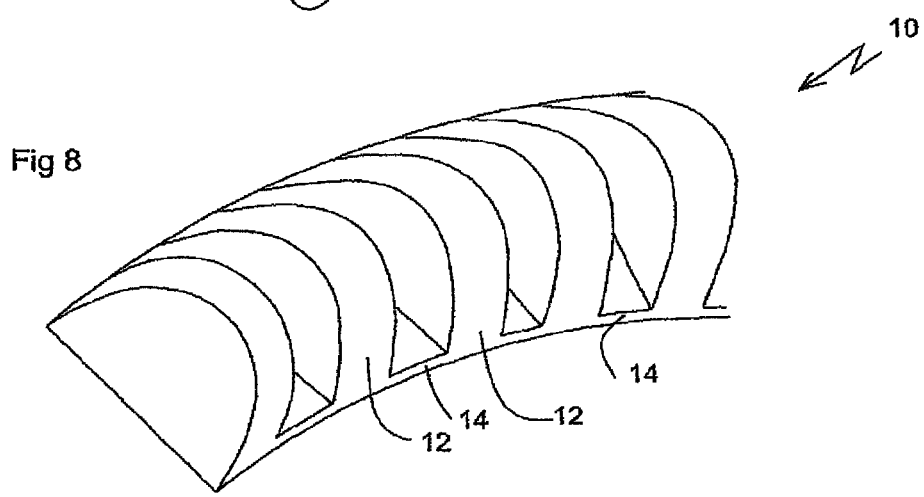
Fig 8
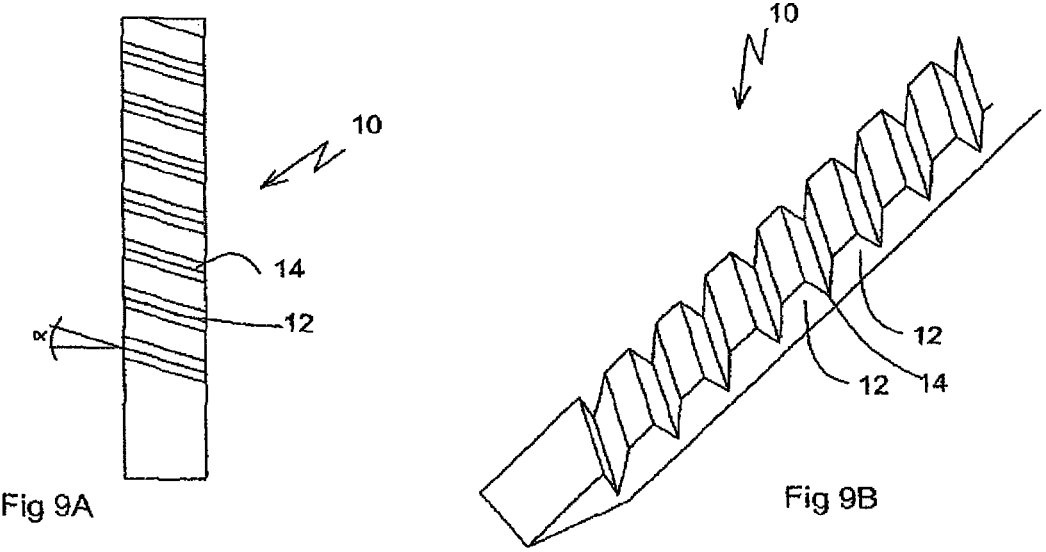
Fig 9A
Fig 9B

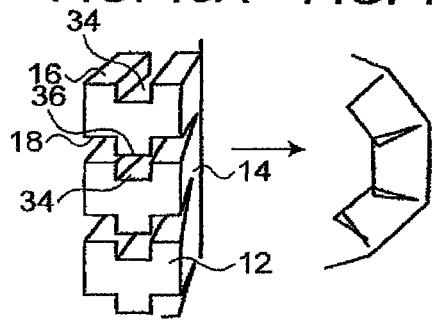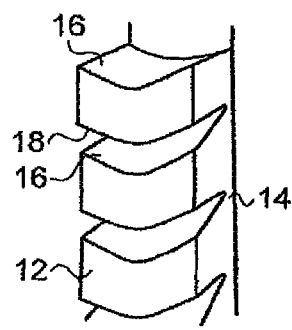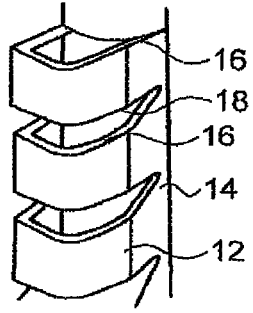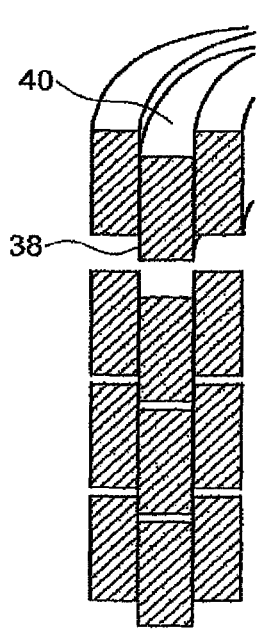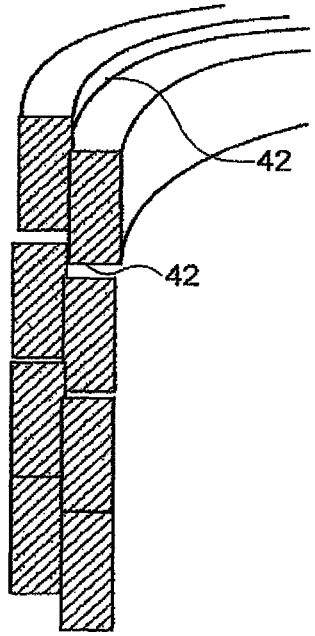

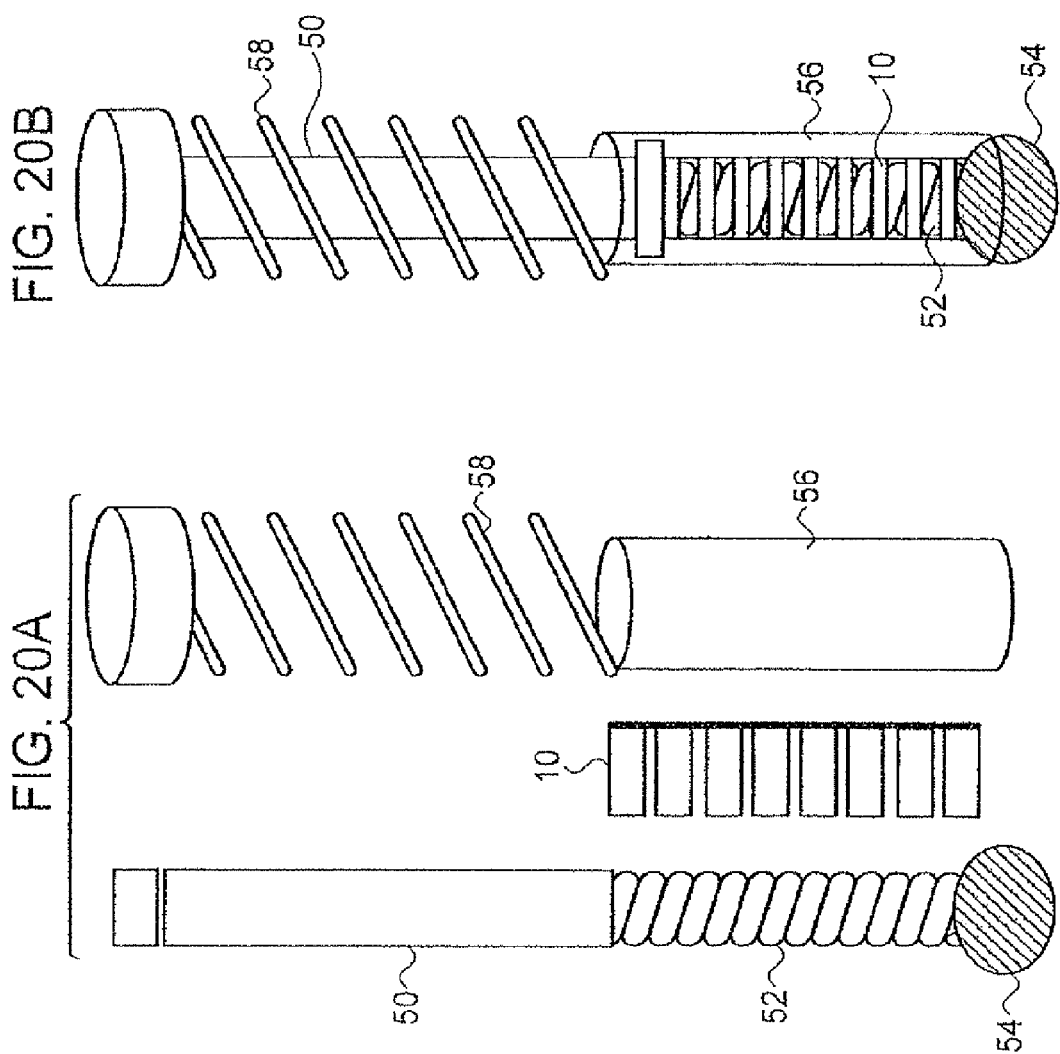

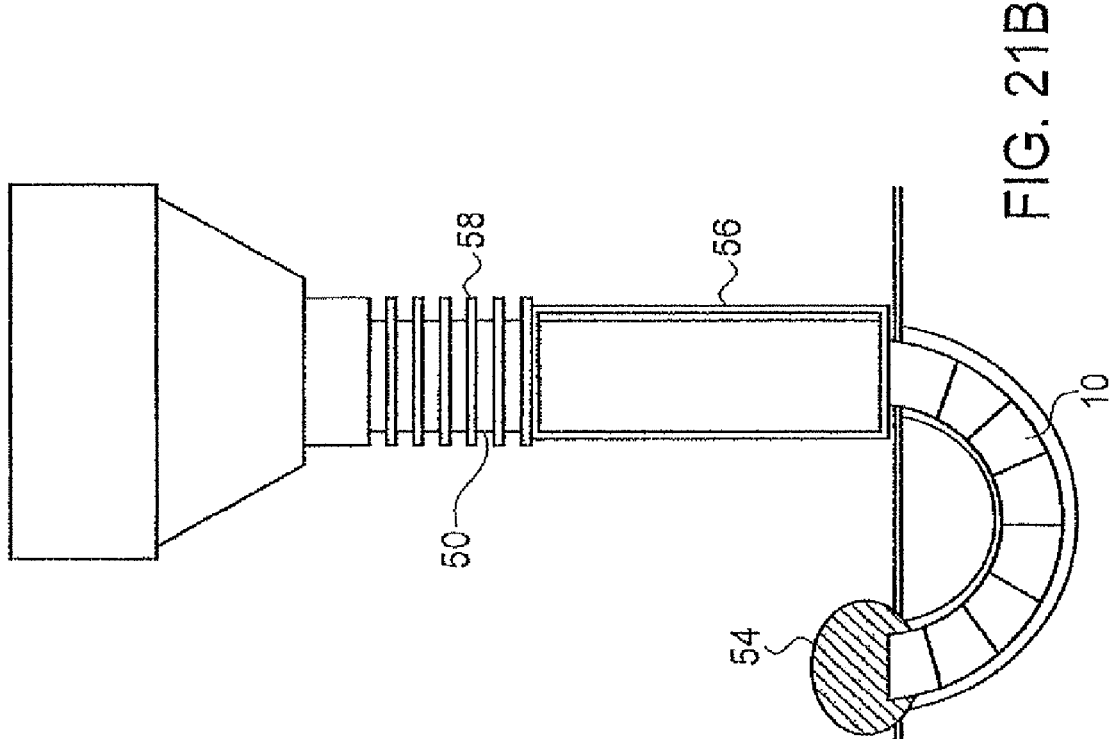
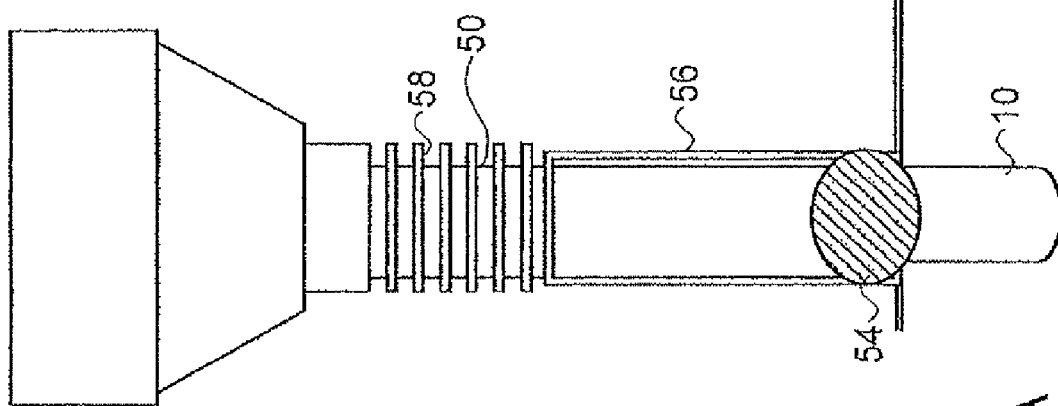
FIG. 21A
FIG. 21B

DEVICES FOR INTRODUCTION INTO A BODY VIA A SUBSTANTIALLY STRAIGHT CONDUIT TO FORM A PREDEFINED CURVED CONFIGURATION, AND METHODS EMPLOYING SUCH DEVICES

This is a continuation of application Ser. No. 12/960,503 filed Dec. 5, 2010, which is a continuation of application Ser. No. 11/813,213 filed Jul. 2, 2007, now issued as U.S. Pat. No. 7,918,874, which is a national stage entry of Application No. PCT/IL05/001393 filed Dec. 28, 2005, which is both a continuation-in-part of application Ser. No. 11/028,655 filed Jan. 5, 2005, now issued as U.S. Pat. No. 7,503,920, and claims priority from Provisional Application No. 60/689,570, filed Jun. 13, 2005.

FIELD AND BACKGROUND OF THE INVENTION

The present invention relates to devices for introduction into a body via a substantially straight conduit to form a predefined curved configuration, and methods employing such devices.

It is known to insert straight elements into various types of bodies. In the general field of mechanical engineering, this includes insertion of drills, nails, screws and rods of various kinds into structures such as walls, articles such as furnishings, other inanimate bodies, plant bodies such as wood, and animal or human bodies. In certain cases, the straight elements have structures or mechanisms for securing the elements against withdrawal from the body.

It is also known in certain contexts to insert elements with a fixed degree of curvature into a body. Examples of this kind include curved needles such as are used for sewing leather, and arcuate drills for medical applications, such as described in U.S. Pat. No. 4,312,337 to Donohue and U.S. Pat. No. 4,941,466 to Romano. Such structures are limited to a very superficial depth of penetration into the body, and generally channel through an arc of less than 180° within the body.

In a third group of applications, primarily limited to the field of medical endoscopy, steerable flexible elements are introduced into a body. Steerable flexible elements can be introduced through straight conduits and can then be deflected within the body in order to steer them to a desired location, thereby allowing the elements to reach a location at an arbitrary desired depth within a body. These elements, however, do not generally assume a well defined curved configuration within the body, and typically do not turn through angles of more than about 180°. In many cases, steerable elements are specifically kept away from their mechanical limit of flexing in order to avoid structural damage through over-flexing.

None of the above provide a structure or method through which a curved structure can be introduced into a body via a straight conduit and then assumes a deployed position in a predefined curved configuration within the body, and particularly where the predefined curved structure turns through more than 180°, has a variable curvature and/or assumes a three dimensional (non-planar) geometry.

There is therefore a need for devices for introduction into a body via a substantially straight conduit to form a predefined curved configuration, and methods employing such devices.

SUMMARY OF THE INVENTION

The present invention is a system and method for deploying an implant within a body.

According to an embodiment of the present invention there is provided, a method for deploying an implant within a body, the method comprising the steps of: (a) deploying a conduit to define a first part of a path of insertion for an implant into the body; (b) advancing an implant along the conduit while the implant is in a straightened state; and (c) deploying the implant from the conduit so as to assume a curved state deployed laterally relative to a direction of elongation of the conduit, wherein the conduit has a generally rectangular transverse cross-section, such that an orientation of the conduit defines an orientation of the lateral deployment of the implant.

There is also provided according to an embodiment of the present invention, a method for deploying an implant within a body, the method comprising the steps of: (a) deploying a guide to define a first part of a path of insertion for an implant into the body; (b) advancing an implant along the guide while the implant is in a straightened state; and (c) deploying the implant from the guide so as to assume a curved state deployed laterally relative to a direction of elongation of the guide, wherein the guide has at least two substantially parallel surfaces, such that an orientation of the guide defines an orientation of the lateral deployment of the implant.

According to a further feature of an embodiment of the present invention, the guide is a substantially rectangular conduit.

According to a further feature of an embodiment of the present invention, a transverse cross-section of the implant has a substantially rectangular outer shape.

There is also provided according to an embodiment of the present invention, a system comprising: (a) a guide formed with at least two substantially parallel walls; and (b) an implant for insertion along the guide, the implant comprising at least two interconnected segments, the segments being deflectable from a straightened state to a deflected state in which the implant has a curved form, wherein the implant is temporarily limited to the straightened state during delivery along the guide, the implant being deflected laterally relative to a longitudinal direction of the guide and assuming the deflected state on leaving the guide.

According to a further feature of an embodiment of the present invention, the guide is a rectangular conduit.

BRIEF DESCRIPTION OF THE DRAWINGS

The invention is herein described, by way of example only, with reference to the accompanying drawings, wherein:

FIG. 7 is an isometric view of a third implementation of a device, constructed and operative according to the teachings of the present invention, for introduction into a body via a substantially straight conduit to form a predefined curved configuration, the device having a circular cross-sectional shape;

FIG. 8 is an isometric view of a fourth implementation of a device, constructed and operative according to the teachings of the present invention, for introduction into a body via a substantially straight conduit to form a predefined curved configuration, the device having a semicircular cross-sectional shape;

FIG. 9A is a front view of a fifth implementation of a device, constructed and operative according to the teachings of the present invention, for introduction into a body via a substantially straight conduit to form a predefined curved configuration, the device having oblique effective hinges between adjacent segments;

FIG. 9B is an isometric view of the device of FIG. 9A;

FIGS. 15A and 15B are a partial schematic isometric view, and a partial schematic side view, of part of a device according to the present invention showing an arrangement for interlocking between adjacent segments of the device, the device being shown in its straight and curved states, respectively;

FIGS. 16A and 16B are a partial schematic isometric views of part of a device according to the present invention showing an alternative arrangement for interlocking between adjacent segments of the device, for a solid and hollow device, respectively;

FIGS. 17A and 17B are isometric cut-away views of a device according to the present invention showing an arrangement for interlocking between adjacent coils of a predefined curved shape corresponding to a closed helix;

FIG. 20A is a schematic side view of components of a drill assembly, constructed and operative according to the teachings of the present invention;

FIG. 20B is a schematic side view of the drill assembly of FIG. 20A assembled;

FIG. 20C is a schematic cross-sectional view through the drill assembly of FIG. 20B;

FIGS. 21A and 21B are schematic side views, taken at orthogonal angles, illustrating the operation of the drill assembly of FIG. 20A;

DESCRIPTION OF THE PREFERRED EMBODIMENTS

The present invention is a device for introduction into a body via a substantially straight conduit to form a predefined curved configuration, and methods employing such a device, The principles and operation of devices and methods according to the present invention may be better understood with reference to the drawings and the accompanying description.

By way of introduction, the present invention provides a family of devices all based on a common inventive concept but varying in their specific implementations, and most notably, in the specific predefined curved form which the devices are configured to assume when they are inserted into a body. The devices are defined geometrically by their structure, and mechanically by their properties, but are not limited to use in any specific field of technology or any specific application. These devices will be described below with reference to FIGS. 1-19E. Then, with reference to FIGS. 20A-29C, a small number of exemplary applications employing these devices will be presented, primarily in the field of medical treatment of the human body.

Figure 1:
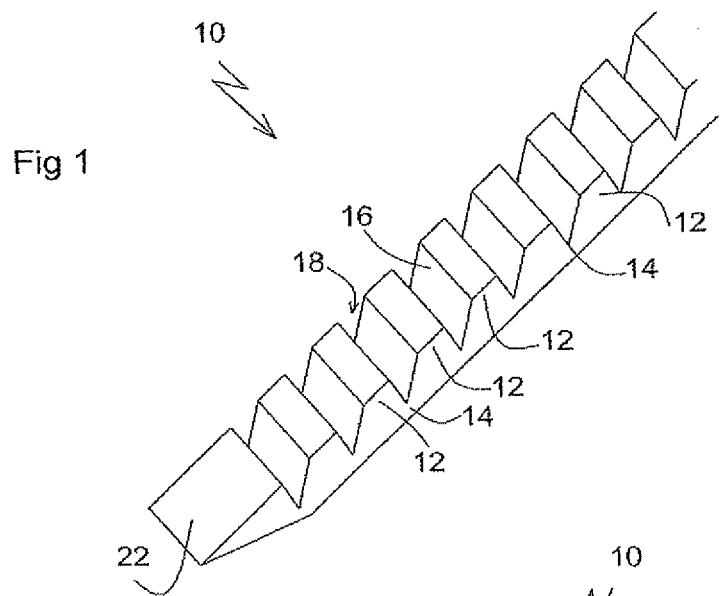
FIG. 1 is an isometric view of a first implementation of a device, constructed and operative according to the teachings of the present invention, for introduction into a body via a substantially straight conduit to form a predefined curved configuration.
Figure 2:
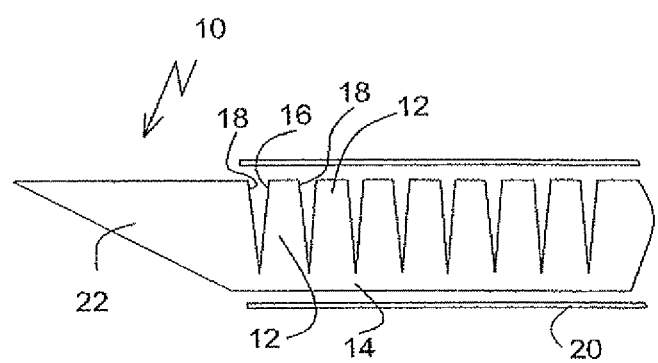
FIG. 2 is a side view of the device of FIG. 1 during insertion along a straight conduit, the conduit being cut-away for clarity of presentation.
Figure 3:
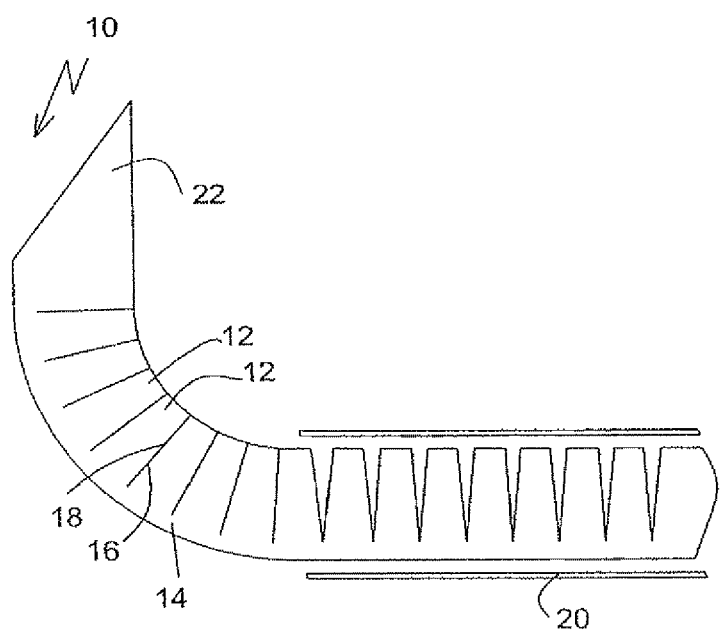
FIG. 3 is a view similar to FIG. 2 showing the device extending beyond the straight conduit and assuming a predefined curved configuration.

Referring now to the drawings, FIGS. 1-3 show a first basic illustration of a device, constructed and operative according to the teachings of the present invention, for introduction into a body via a substantially straight conduit 20, and assuming within the body a predefined curved configuration.

In general terms, the device of each embodiment of the present invention includes an elongated element 10 formed primarily from a plurality of segments 12 sequentially interconnected so as to form an effective hinge 14 between adjacent segments 12. Segments 12 and effective hinges 14 are configured such that: (a) when the elongated element 10 is confined to a substantially straight state, effective hinges 14 transfer compressive forces from each segment 12 to the next so that the elongated element 10 can be pushed so as to advance through substantially straight conduit 20; and (b) when elongated element 10 is not confined to a substantially straight state, effective hinges 14 allow deflection of each segment 12 relative to adjacent segments 12 until at least one abutment surface 16 of each segments comes into abutment with at least one corresponding abutment surface 18 of each adjacent segment, thereby defining a fully flexed state of elongated element 10 corresponding to a predefined curved configuration of the elongated element.

It will immediately be clear that the device of the present invention thus defined is capable of insertion into a body to any desired depth, since it initially follows a substantially straight path, and then deploys within the body to form a predefined curved structure in which adjacent segments are interconnected at an effective hinge and abut via at least one additional surface, thereby providing considerable mechanical stability. Thus, a wide range of curved or convoluted structures can be introduced temporarily or permanently via an insertion opening which has dimensions corresponding to the cross-sectional dimensions of the elongated element making up the final shape.

The devices of the present invention may thus be used for a wide range of applications including, but not limited to: forming a curved channel through a body; cutting-out a sample of material from a body; providing a curved anchoring structure within a body; joining together two parts of a body; aligning two parts of a body; forming a reinforcing structure within a body; filling a region of a body; and expanding a spacing between parts of a body.

The transition from the substantially straight configuration of the device to the predefined curved configuration can be achieved in a number of ways. According to a first set of implementations, elongated element 10 is resiliently biased so as to tend to deflect towards its predefined curved state. This may be achieved through pre-biasing of effective hinges 14 or by addition of supplementary springs or other resilient elements (not shown). In an alternative set of implementations, the geometry of elongated element 10 is chosen such that mechanical resistance during insertion of element 10 into a body causes deflection of the device to its curved state. According to either of the above options, flexing of the device is progressive, occurring continuously as the device is extended beyond the delivery conduit 20. According to a further alternative, a selectively operable mechanism (not shown), such as one or more drawstring, may be provided for allowing a user to selectively induce deflection to the predefined curved configuration.

As already mentioned, the present invention can be used in a wide range of fields of application including, but not limited to, building, mining, industrial applications, carpentry, and medicine. Accordingly, the "body" within which the device is deployed may be any body, including but not limited to: a human body; an animal body; wood; other biological materials; walls; furniture; minerals; and other inanimate objects. Clearly, the dimensions, materials and other design parameters for the device of the present invention must be selected to render it suited to the intended application, as will be clear to one ordinarily skilled in the field of applications for which it is to be used.

Turning now to structural features of specific implementations of the device of the present invention, elongated element 10 as illustrated in FIG. 1 is preferably formed from a single elongated rod of rectangular cross-section from which a series of transverse slots are cut to subdivide the elongated element into segments 12. The relatively thin connecting bridge of material left beneath the slots renders the interconnections flexible, thereby providing effective hinges 14. The slots are shown here as V-shape slots, corresponding to sloped end surfaces of segments 12. Other slot shapes, such as U-shaped slots, rectangular slots, and more complex shaped slots, may also be used.

It will be appreciated that the structure shown provides all the structural features of the device of the present invention in a very straightforward and easily manufactured manner, simply by fanning appropriately shaped and positioned slots in a rectangular rod. Effective hinges 14 are thus integrally formed as flat connecting portions of flexible material interconnecting between adjacent segments. The term "flat" is used in this context to refer to the cross-sectional shape, namely, that in cross-section along the effective axis of the hinge, the thickness of the integral hinge is significantly less than its width, thereby providing a well-defined direction of flexing. The integral hinge may have significant length extending between segments 12 (as illustrated in certain examples below) or may have minimal length (such as illustrated here). Effective hinges 14 preferably provide resistance to relative motion of adjacent segments 12 other than the intended binged motion, thereby avoiding unwanted torsional deformation of elongated element 10.

Clearly, if the device is constructed by cutting slots in an initially straight rod of material, and unless the elongated element is further treated to change its properties, the unstressed state of the elongated element will be in the straightened configuration. According to a particularly preferred option illustrated here, elongated element 10 terminates in a beveled distal tip 22 angled so as to tend to deflect the elongated element into the fully flexed state as the elongated element advances through a medium. Specifically, the beveled distal tip 22 preferably has a leading edge on the side from which the slots are cut and a bevel surface facing away from the side of slots. This shape, when advanced into a compressible or displaceable medium, tends to be deflected so as to follow a curved path, thereby bending elongated element 10 progressively towards its fully flexed curved form as it advances beyond delivery conduit 20, as shown in FIG. 3.

The dimensions of the device of the present invention are chosen according to the intended application and the required predefined curved shape which is to be formed. Thus, at one extreme, for use in hollowing out a subterranean tunnel or an underwater tunnel, an element with a width and height of one meter or more may be used. At the other extreme, certain delicate medical applications may use an elongated element with a width and height of 5 millimeters or less. For a wide range of domestic and medical applications, lateral dimensions of 1-30 mm are suitable.

In terms of relative dimensions, elongated element 10 is termed "elongated" in the sense that its length is significantly longer than both its width and its height. Most preferably, a length of elongated element 10 is at least ten times greater than each transverse dimension (height and width) of the elongated element. Preferably, the device is configured to form a predefined curved configuration including an arc turning through an angle of at least 180°, and in many cases, passing through one or more complete revolutions as will be illustrated in a number of examples below.

The materials for the device of the present invention are also chosen according to the intended application and the mechanical and other properties which are required, and may be any suitable materials. For many applications, various metals and metal alloys (referred to collectively as metallic materials) are suitable. For some applications, various plastics and other polymer materials are suitable. Other possibilities include, but are not limited to, composite materials and ceramic materials. For medical applications, biocompatible are used, typically either metallic materials or polymers such as PEEK.

It will be noted that the terms "two-dimensional" and "planar" are used to refer to the geometry of the predefined curved configuration of certain embodiments such as those of FIGS. 1-8 and 11-12C, whereas the terms "three-dimensional" and "non-planar" are used to refer to the geometry of the predefined curved configuration of embodiments such as those of FIGS. 9A-10, 13 and 14. These terms are used to classify the nature of the curvature exhibited, i.e., that a circle or flat spiral is a "planar" geometry whereas a helix or cone is a "non-planar" geometry. Clearly, even the "planar" geometry implementations also occupy space in three dimensions due to the width of the elements.

In the example of FIGS. 1-3, elongated element 10 is cut from a solid rod such that each segment 12 is formed as a non-hollow block of material. Although the unitary construction with the effective hinges 14 integrally formed with the segments 12 is believed to be advantageous, it should be noted that alternative implementations of effective hinges 14 also fall within the scope of the present invention. By way of example, a first alternative implementation employs a flexible strip as a backbone for the device to which segments 12 (separate blocks) are attached by any suitable attachment technique. An example of this kind is illustrated below with reference to FIGS. 19a-19E. A second alternative implementation employs a pivotal interlocking hinge arrangement, of a type either with or without a hinge pin, for connecting between initially separate segments 12.

Substantially straight conduit 20 may be any suitable conduit, preferably close-fitting to the external shape of elongated element 10 in its substantially straight configuration. Conduit 20 may be made of similar materials to elongated element 10, or may be made from any other materials which are compatible with the intended application. Furthermore, although conduit 20 is the preferred example of a structure for restricting elongated element to a substantially straight configuration during a first part of insertion into a body, it should be noted that other alternatives also fall within the general scope of the present invention. Thus, for example, in hollow implementations (such as will be described below with reference to FIGS. 4-6), an equivalent effect may be achieved using a centrally deployed rail passing at least partially within elongated element 10 which restricts a part of elongated element 10 to its straight configuration.

Figure 4:
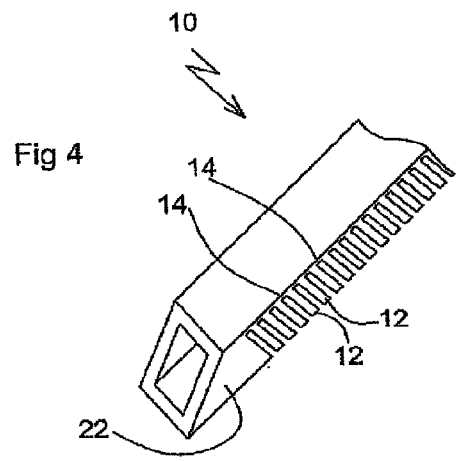
FIG. 4 is an isometric view of a second implementation of a device, constructed and operative according to the teachings of the present invention, for introduction into a body via a substantially straight conduit to form a predefined curved configuration, the device having a hollow central channel.
Figure 5:
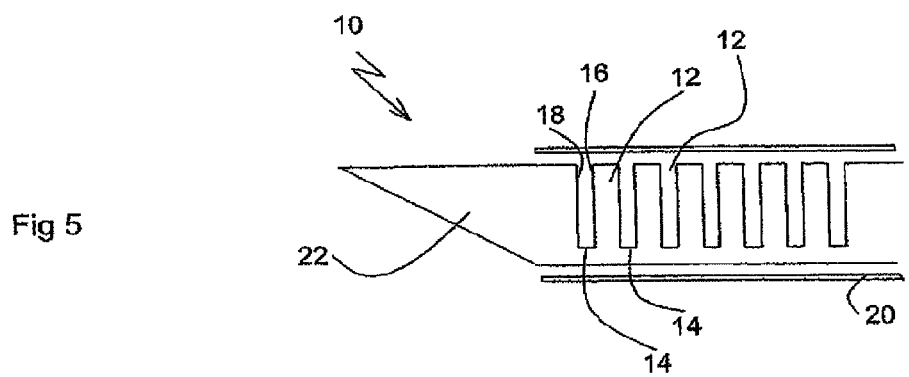
FIG. 5 is a side view of the device of FIG. 4 during insertion along a straight conduit, the conduit being cut-away for clarity of presentation.
Figure 6:
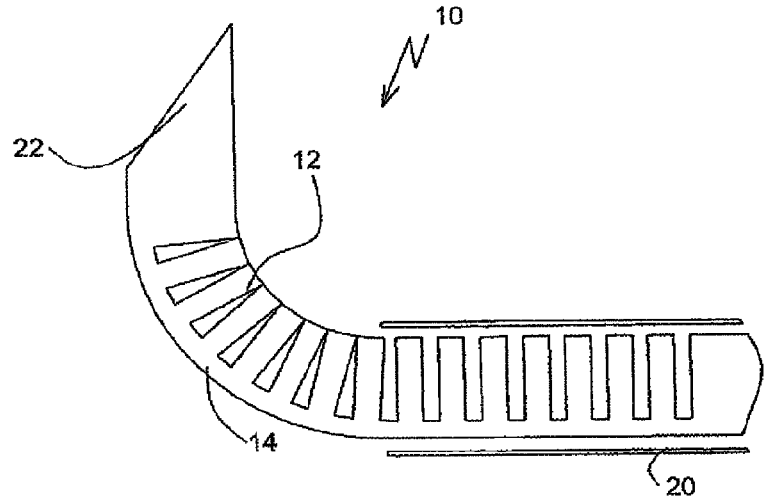
FIG. 6 is a view similar to FIG. 5 showing the device extending beyond the straight conduit and assuming a predefined curved configuration.

Turning now to FIGS. 4-6, these show a second implementation of the device of the present invention. This implementation is generally similar to that of FIGS. 1-3, differing in two respects, as will now be detailed.

Firstly, in this implementation, the slots are formed as rectangular slots, so that the abutment surfaces 16 and 18 are only along the upper edges of the adjacent segments. This form has certain advantages of simplicity of manufacture, and is also less sensitive to the presence of foreign matter between the abutment surfaces interfering with the curved configuration. On the other hand, the curved structure has triangular lateral openings between adjacent segments which may be undesirable for certain applications.

Secondly, this implementation is formed from a hollow rod, resulting in an elongated element 10 in which each segment 12 is a hollow block of material. The resulting central channel through elongated element 10 may be useful for a wide range of functions, including but not limited to: cutting out a sample of material from a body; excavating a volume of material from a body; insertion of a flexible tool through elongated element 10 to reach a target location within a body; delivering a quantity of fluid or other material to a target location within a body; providing a drive shaft for a drilling tool or other tool located at the distal end of elongated element 10; relaying illumination and/or images to/from a target location within a body; filling with cement to fix a deployed configuration of elongated element 10; and filling elongated element 10 with other materials for imparting desired properties to elongated element 10 or surrounding regions of a body.

In all other respects, the structure and function of the implementation of FIGS. 4-6 can be fully understood by analogy with the structure and function of the implementation of FIGS. 1-3 described above.

Turning now to FIGS. 7 and 8, it should be noted that elongated element 10 may be implemented with a wide range of different cross-sectional shapes. Thus, by way of examples, FIG. 7 shows an implementation in which elongated element 10 is substantially circular in cross-section. In this case, effective hinges 14 are preferably formed as integral hinges by leaving a portion corresponding to a chord of the circle bridging between adjacent segments 12. FIG. 8 shows an implementation in which elongated element 10 is substantially semi-circular. Effective hinges 14 interconnecting segments 12 are preferably formed at the flat side of the elongated element.

Figure 10:
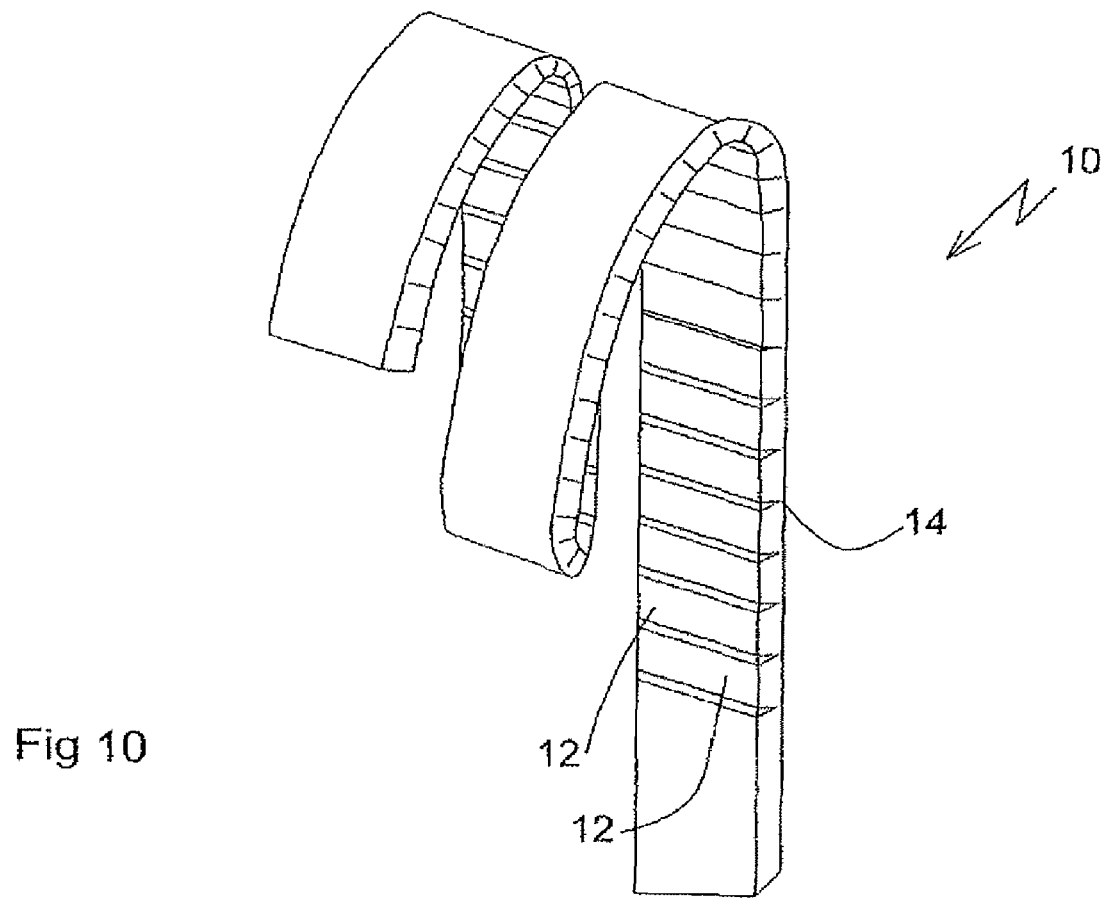
FIG. 10 is a view similar to FIG. 9A showing the device in its predefined curved configuration.

Turning now to FIGS. 9A, 9B and 10, these illustrate an implementation of the device of the present invention generally similar to that of FIGS. 1-3 but wherein the predefined curved configuration is a helix. To achieve this result, the slots between adjacent segments 12, and therefore the axes of effective hinges 14, are at an oblique angle relative to a direction of elongation of elongated element 10. This is seen most clearly in the plan view of FIG. 9A where angle a denotes the inclination of the effective hinge axes relative to a line perpendicular to the direction of extension of elongated element 10. The result of this oblique angle of the effective hinges 14 is that the predefined curved configuration includes a lateral component of curvature, thereby forming a helix as shown in FIG. 10. Varying angle of inclination a varies the pitch of the helix, so that the helix can be designed to be either open as shown (i.e., with space between adjacent coils of the helix) or closed (i.e., where adjacent coils touch each other).

Figure 11:
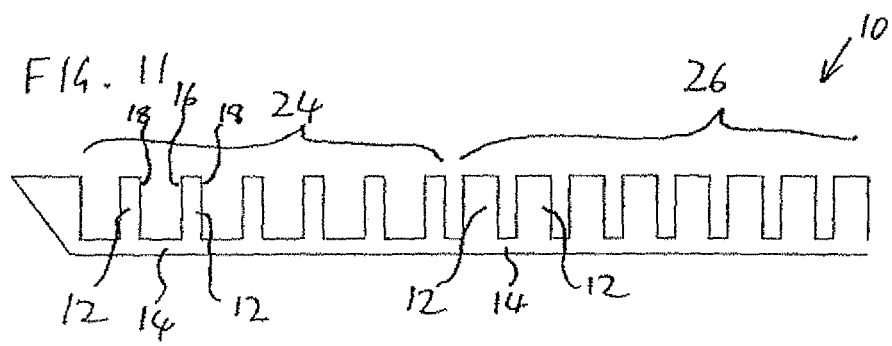
FIG. 11 is a side view of a sixth implementation of a device, constructed and operative according to the teachings of the present invention, for introduction into a body via a substantially straight conduit to form a predefined curved configuration, the device having a first region configured to produce a predefined curved configuration with a first radius of curvature and a second region configured to produce a predefined curved configuration with a second radius of curvature.

Turning now to FIGS. 11 and 12A-12C, it should be noted that the predefined curved configuration of the devices of the present invention does not have to be a uniform configuration with constant curvature along the length of elongated element 10. Thus, by way of example, FIG. 11 illustrates an elongated element 10 which produces a predefined curved configuration (visible in FIG. 12C) including a first region 24 having a first radius of curvature $R_1$ and a second region 26 having a second radius of curvature $R_2$ greater than $R_1$. To achieve this result, the size of segments 12 and their spacing are varied between regions 24 and 26 so that a greater degree of deflection occurs between adjacent segments 12 and/or the segments are more closely spaced in region 24.

Figure 12A:
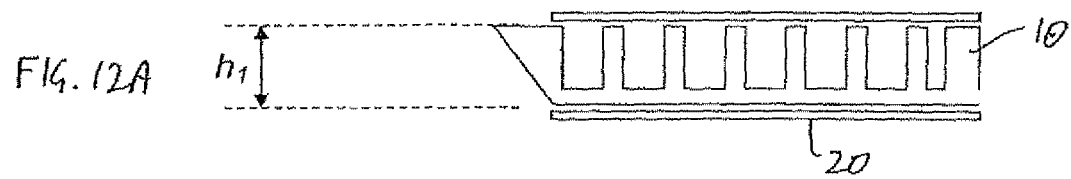
FIGS. 12A, 12B and 12C are side views of the device of FIG. 11 at three stages during insertion along a straight conduit, the conduit being cut-away for clarity of presentation.
Figure 12B:
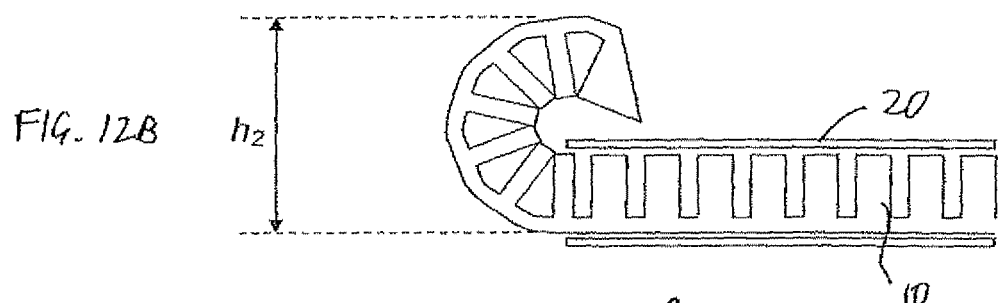
Figure 12C:
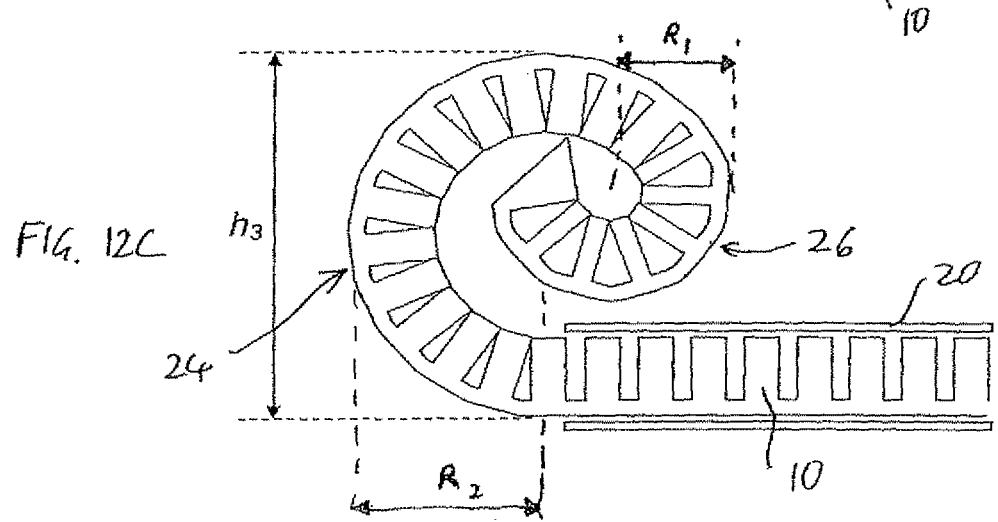

FIGS. 12A-12C illustrate the sequence of deployment of the device of FIG. 11 as it is advanced from conduit 20. As the distal tip of elongated element 10 first advances beyond conduit 20, it occupies a height dimension $h_1$ corresponding substantially to the corresponding dimension of the device in its substantially straight configuration. (The up-down dimension as illustrated is referred to here for convenience as "height" although the device can clearly be used in any orientation.) As it advances, region 24 starts to assume its predefined curved configuration, thereby defining a part of a substantially circular form of diameter (and hence height) $h_2$ which is twice the smaller radius of curvature $R_1$. Then, as elongated element 10 is advanced further, region 26 progressively extends beyond conduit 20 to form an arc of radius $R_2$, and hence raising the overall height to $h_3$ (twice $R_2$). The overall effect is gradual opening of a shape which is referred to herein as a spiral. Clearly, this effect could be continued, for example by forming a third region of elongated element 10 with more closely spaced segments configured to provide a yet larger radius of curvature.

It will be noted that the gradual increase in the effective height of the device, and in particular, during the transition from $h_2$ of FIG. 12B to $h_3$ of FIG. 12C, renders the device useful as a mechanism for lifting a part of a body, or for separating between two parts of a body. An example of such an application will be illustrated below.

It will be noted that the term "spiral" is used herein in its colloquial sense to refer to any shape which spirals inwards/outwards, and is not limited to a geometric spiral which is referred to herein as a "perfect spiral". The spiral formed from a stepped increase in radius of curvature as described here may be preferred due to its simplicity of manufacture. Nevertheless, it will be appreciated that it is possible to vary segment size and/or inter-segment spacing in a continuous manner to achieve a close approximation to a perfect spiral, or any other varying curvature profile desired.

Figure 13:
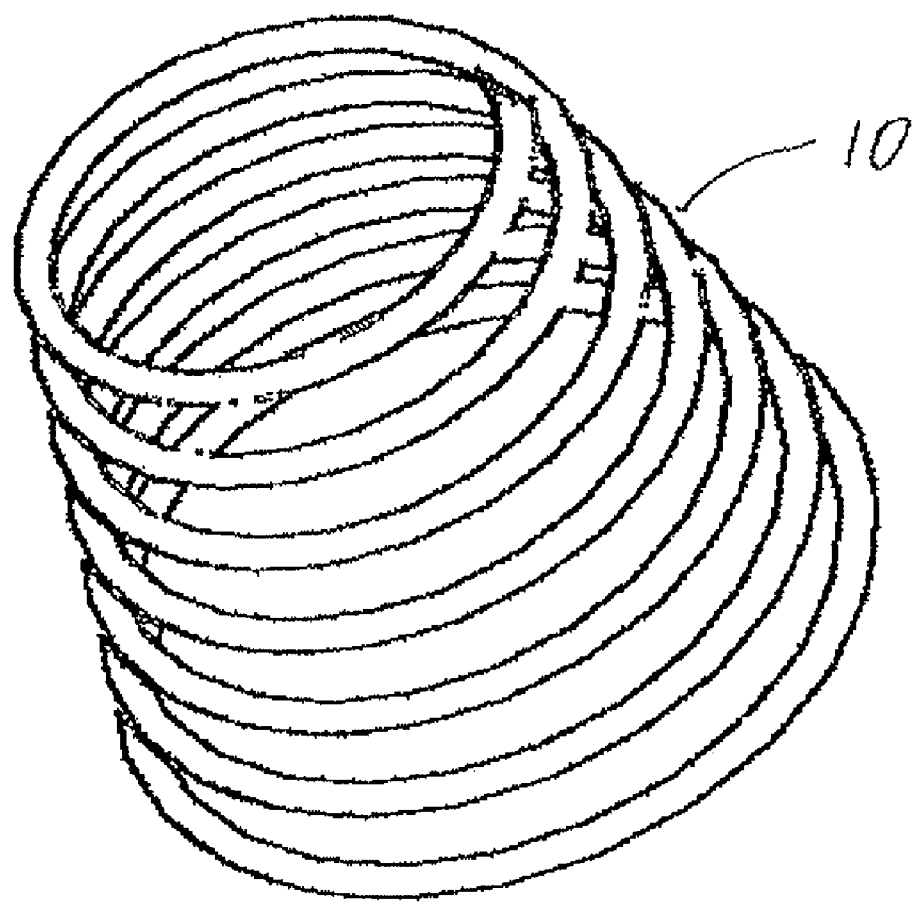
FIG. 13 is an isometric view of a seventh implementation of a device, constructed and operative according to the teachings of the present invention, for introduction into a body via a substantially straight conduit to form a predefined curved configuration, the device having a predefined shape corresponding to a conical helix.
Figure 14:
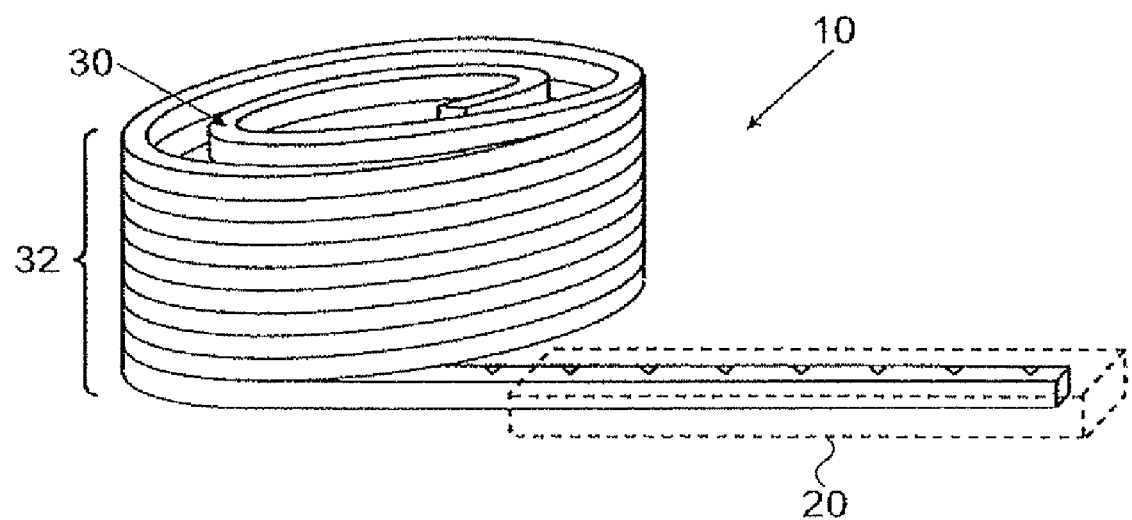
FIG. 14 is a front view of an eighth implementation of a device, constructed and operative according to the teachings of the present invention, for introduction into a body via a substantially straight conduit to form a predefined curved configuration, the device having a predefined curved shape including both a flat spiral with a closed cylindrical helix.

Turning now to FIGS. 13 and 14, it should be noted that the principles of lateral progression described above with reference to FIGS. 9A-10 and of variable curvature described above with reference to FIGS. 11-12C can be combined to achieve an effectively unlimited range of convoluted three-dimensional structures in which radius of curvature and axial progression are arbitrarily chosen according to a specific desired application. FIGS. 13 and 14 illustrate two examples of particular importance which combine these principles.

Specifically, FIG. 13 illustrates schematically a predefined curved configuration of an elongated element 10 which is formed as a conical spiral, i.e., a series of coils with sequentially increasing radius of curvature combined with axial progression. As before, the variation of the radius of curvature may be either continuous (i.e., varying between each adjacent pair of segments) or may be varied in steps, such as every few segments, or every 90° or 180° of a coil.

FIG. 14 shows a further preferred example in which a distal part of elongated element 10 is configured to foam a planar spiral 30 (similar to FIG. 12C) and a second portion of elongated element 10 forms a helix 32. In this case, helix 32 is preferably a closed helix, i.e., where each coil sits in contact with the adjacent coils (referred to as "stacked coils"). This contact between coils renders the shape structurally strong so that the device can be used for lifting part of a body or separating between two parts of a body, even where considerable forces are involved. At the same time, the presence of the planar spiral at the distal end ensures that a flat surface contacts the body to be lifted, thereby avoiding heavy abrasion of the lifted body by the leading end of the elongated element. An application of this implementation of the device will be described below.

Turning now to FIGS. 15A-17B, it will be noted that various modifications of the shape of segments 1.2 may be made in order to provide various forms of interlocking, thereby improving mechanical stability of the predefined curved configurations of the present invention. Thus, FIGS. 15A and 15B show one possible modification in which abutment surfaces 16 and corresponding abutment surfaces 18 are configured with interlocking features such that, in the fully flexed state of FIG. 15B, the interlocking features help resist torsional deformation of the elongated element. In the example shown here, abutment surfaces 16 are formed with slots 34 while complementary abutment surfaces 18 are formed with projecting ridges 36 configured for engaging slots 34.

FIGS. 16A and 16B illustrate the same concept implemented without sharp ridges and slots, but rather with concavely and convexly curved abutment surfaces 16 and 18. FIG. 16B illustrates the same structure as FIG. 16A implemented in a hollow embodiment.

Turning now to FIGS. 17A and 17B, these illustrate an additional option specifically for closed helical forms such as helix 32 of FIG. 14 in order to further stabilize the resulting stack of coils. According to this feature, lateral surfaces of segments 12 are formed with complementary interlocking features so as to inhibit lateral displacement of successive coils of the helix. In the example of FIG. 17A, these complementary interlocking features are implemented as such as ridges 38 and slots 40. In the example of FIG. 17B, a single step or shoulder 42 is provided. This second option is also useful for stabilizing a closed conical spiral where the difference in radial dimensions between adjacent coils is equal to the width of the single step.

Figure 18A:
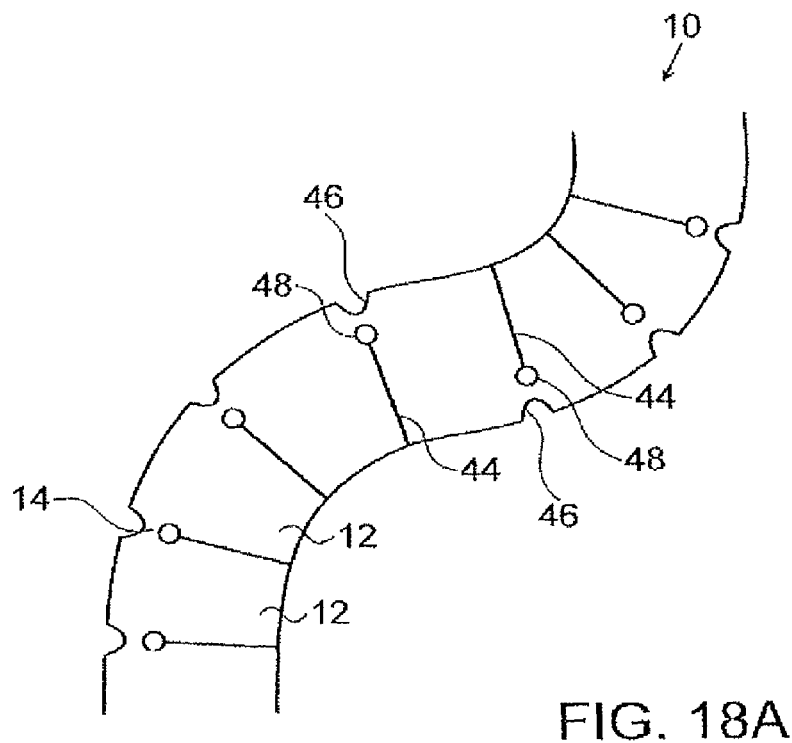
FIGS. 18A and 18B are schematic partial side views of a device according to the present invention in its predefined curved shape and its straightened shape, respectively, showing an implementation of hinged interconnection for an arbitrarily curved shape.
Figure 18B:
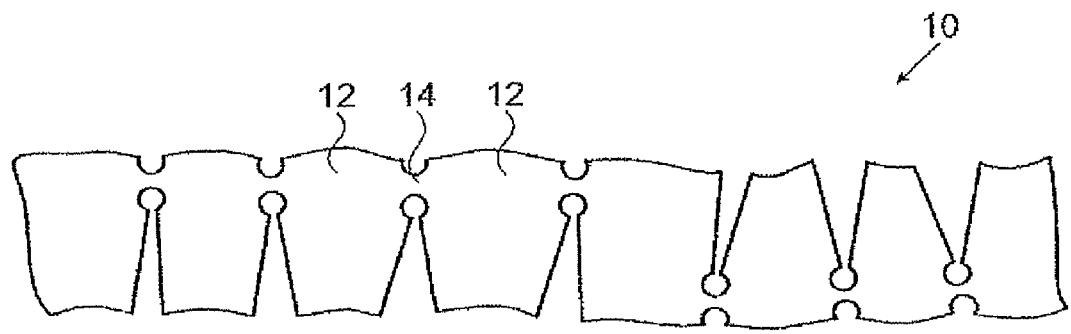

Turning now to FIGS. 18A and 18B, these illustrate schematically an alternative approach to implementing the device of the present invention which facilitates fowling elongated elements with arbitrarily shaped predefined curved configurations in two or three dimensions, and which are biased to their curved configurations. Specifically, according to this approach, an elongated element, typically having a uniform cross-section, is first formed into the desired predefined curved configuration by known techniques. These may include wire or bar shaping techniques for metallic material, and molding or extrusion for polymer materials. For three-dimensional shapes, a round cross-section is typically preferred. The elongated element is then cut to form a plurality of slits 44 from the inside of the local curvature of the element outwards and, in the case of a round cross-section, a corresponding clearance channel 46 from the opposite side of the element. Most preferably, a round bore 48 is formed at the base of each slit 44 to spread stresses within the material. This structure thus defines an elongated element 10 with a plurality of segments 12 formed between slits 44 and effective hinges 14 formed between bores 48 and clearance channels 46, allowing the element to be opened up to a substantially straight configuration as shown in FIG. 18B. Although the example shown here for simplicity of visual representation is a two-dimensional form with curvature reversal, it will be appreciated that the curvature, and the corresponding hinge axis directions defined by slits 44 and clearance channels 46, can be rotated at arbitrarily chosen angles, allowing substantially any three-dimensional curved shape to be produced. The resulting structures can be opened up to a substantially straight configuration as required, but are naturally pre-biased to return to their predefined curved configuration.

Figure 19A:
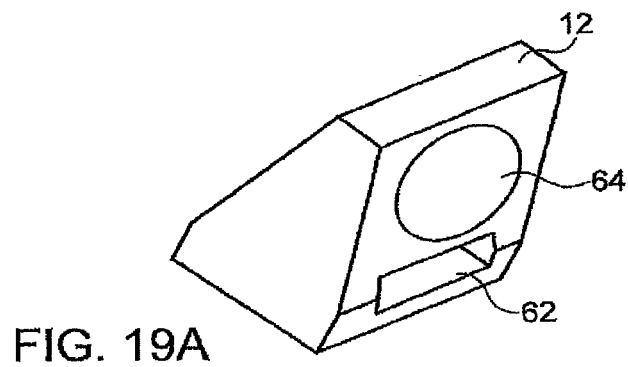
FIGS. 19A-19C are schematic isometric, longitudinal cross-sectional and end views, respectively, of an individual segment for use in a further implementation of a device according to the teachings of the present invention.
Figure 19B:
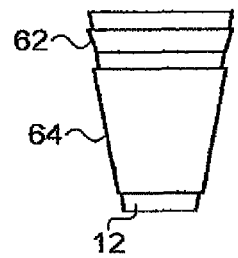
Figure 19C:
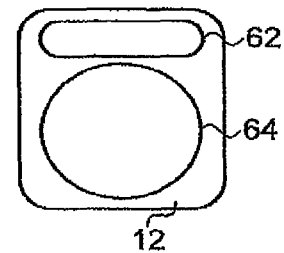
Figure 19D:
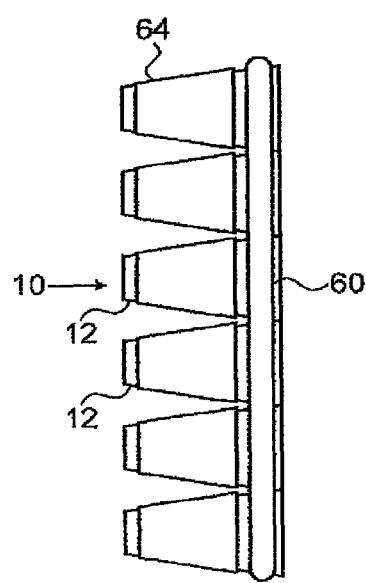
FIGS. 19D and 19E are schematic longitudinal cross-sectional views of a device fowled from a plurality of the segments of FIGS. 19A-19C, the device being shown in its straightened state and predefined curved shape, respectively.
Figure 19E:
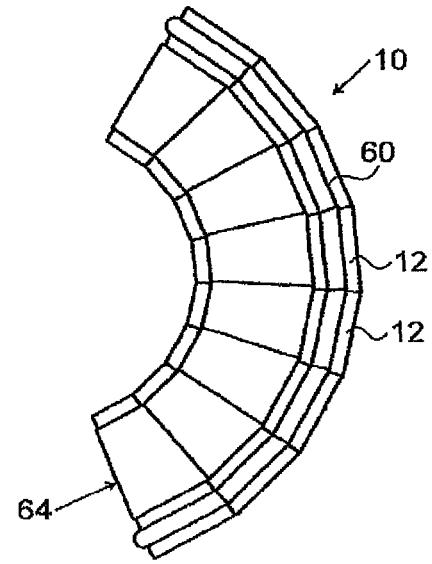

Turning now to FIGS. 19A-19E, as mentioned earlier, the devices of the present invention may be implemented using a wide variety of structures for segments 12 and effective hinges 14. By way of a further non-limiting example preferred for certain applications, FIGS. 19A-19C show an implementation of a segment 12 formed as a separate block, and FIGS. 19D and 19E show an elongated element 10 formed from a series of such blocks positioned in abutment along a sheet-spring element 60. The sheet spring 60 passes through channels 62 formed in each segment 12, thereby aligning the segments. The sheet spring is preferably pre-biased to a curved form so that it returns resiliently to the curved form of FIG. 19E and can be straightened to the form of FIG. 19D. In the example shown here, each segment 10 further features a substantially cylindrical central opening 64, openings 64 being aligned in the elongated element to form a "hollow" element in the sense used above. This round central channel is particularly suited to applications such as the flexible drill shaft described below with reference to FIGS. 20A-21B.

Turning now to applications for the devices of the present invention, it should be noted that the invention may be used in any situation where it is useful to provide a structure with a predefined curved shape which can be straightened into an elongated structure for convenient delivery, such as along a conduit. Examples of types of application for which the present invention is useful include, but are not limited to: tunneling or drilling to form a channel; extracting material; anchoring to a body; clamping together two bodies; providing a reinforcing structure; as a filler structure; as an expander; and as a medical implant.

Depending upon the physical properties of the body into which the device is introduced, the device may form its own channel by one or more process including compacting material, displacing material, or, in the case of hollow embodiments such as in FIGS. 4-6, cutting out a core of material which enters the hollow of the device. Optionally, a mechanism (not shown) may be provided for mechanically advancing the device into the material. In other cases, it may be necessary or preferable to provide the device with active drilling capabilities. One configuration suitable for implementing the present invention in combination with a drill is illustrated schematically in FIGS. 20A-21B.

Thus, turning to FIGS. 20A-20C, these show a curve-drilling attachment, implemented according to the teachings of the present invention, for use with a conventional or slightly modified drill. The attachment includes a rotating drill element 50 formed from a rotatable drive shaft of which at least a portion 52 is flexible and which terminates in a drilling burr 54. The flexible portion 52 of the shaft may be implemented as a helical spring as shown, or as various other flexible drive element effective for transferring rotational power to the drilling burr. The drill element 50 is located within a hollow implementation of elongated element 10 which is anchored around flexible portion 52 but does not rotate. Around elongated element 10 is an outer conduit 56 which is urged by a spring 58 towards drilling burr 54. As visible in FIG. 20C, the elongated element 10 and outer conduit 56 of the preferred embodiment shown here are implemented with rectangular cross-sections.

FIGS. 21A and 21B illustrate the operation of the drill attachment. As the drill is advanced into a body, outer conduit 56 is held back, either by being too large to follow the drill element into the hole or due to a flange (not shown) located to define a straight-drilling depth. Once outer conduit 56 stops advancing, subsequent advancing of the drill element 50 allows the portion of elongated element 10 beyond the conduit to assume its predefined curved configuration, in this case an arc of a circle, thereby bending the flexible portion 52 so that drilling burr 54 follows an arcuate path as seen in FIG. 21B. It should be noted that a drill attachment and corresponding drilling method according to these principles may be used in a wide variety of applications. For example, in household applications, arcuate drilled channels may be used for anchoring to a wall or other object. Similarly, in dental applications, this form of drilling may be important for anchoring implants within bone. Other non-limiting examples of applications will be discussed below.

Parenthetically, it will be noted that this drilling technique can be used for drilling more complex three-dimensional structures. For example, if a helical hollow elongated element is used, it is possible to drill a helical bore through solid material. Such a bore may be valuable for various applications, including but not limited to, forming a helical cooling channel for pumping a coolant within a cylindrical wall of a cylinder.

Figure 22C:
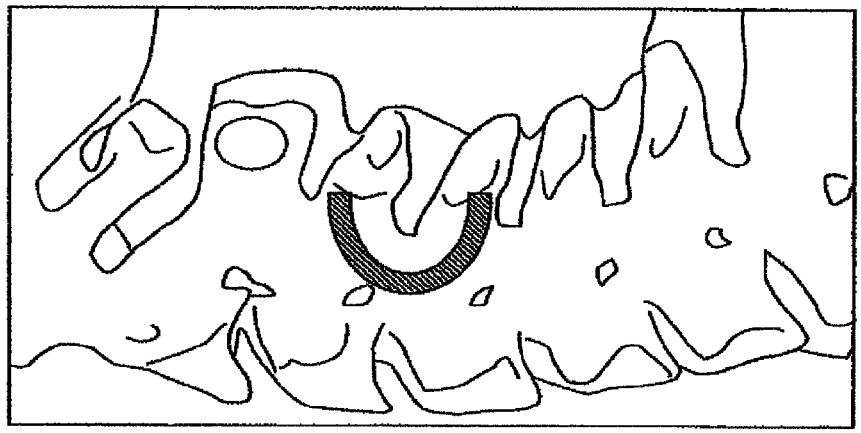
FIGS. 22A-22C are schematic illustrations of an implementation of the present invention for posterior cervical bone anchoring using quadru-cortical bone engagement.
Figure 22B:
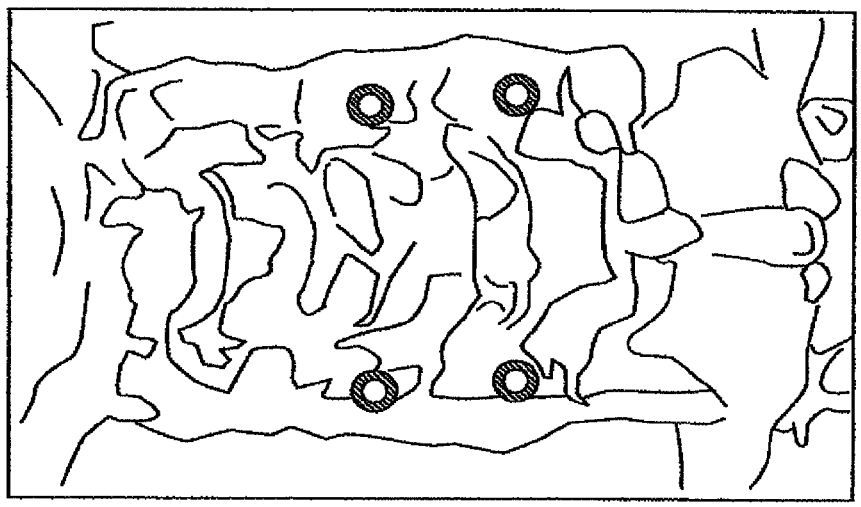
Figure 22A:
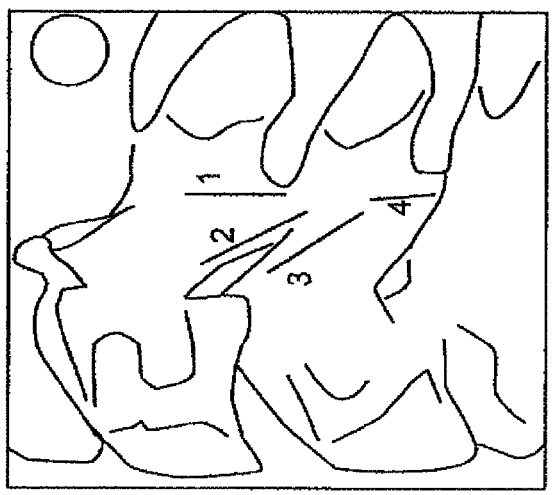
Figure 23C:
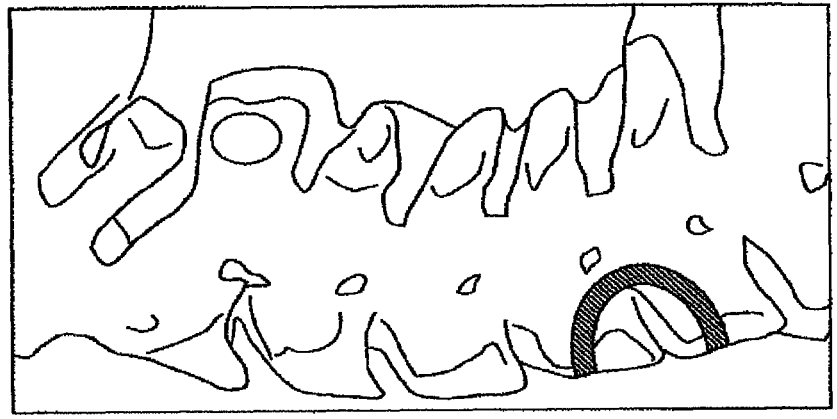
FIGS. 23A-23C are schematic illustrations of an implementation of the present invention for anterior cervical bone anchoring using quadru-cortical bone engagement.
Figure 23B:
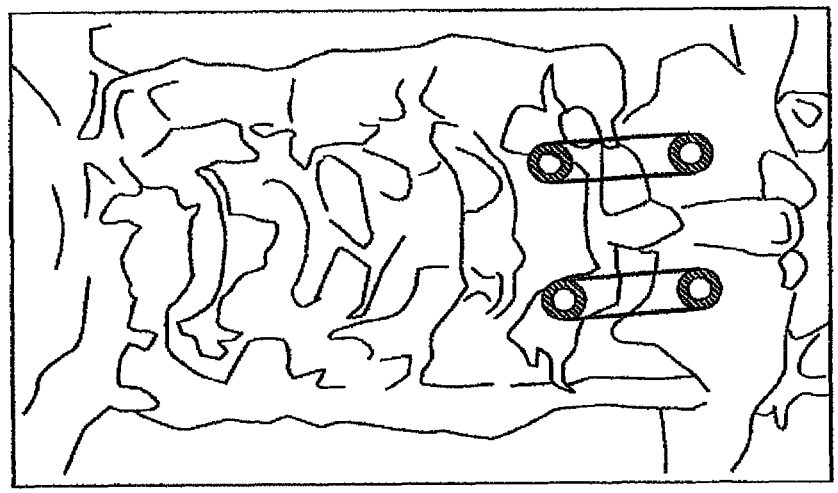
Figure 23A:
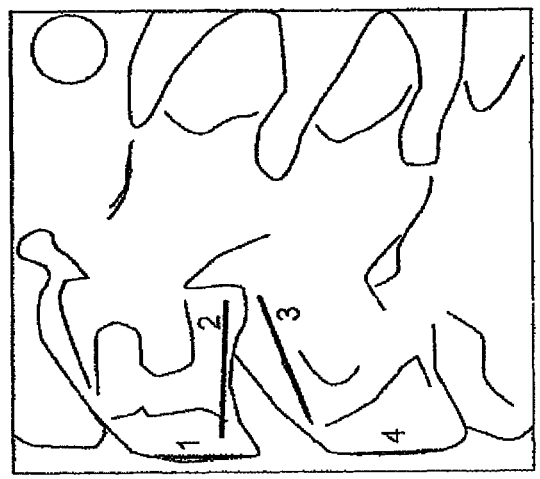

Turning now to FIGS. 22A-22C and 23A-23C, these illustrate a further medical application of the arcuate drilling technique of the present invention for providing bone anchoring. Particularly, the examples illustrated in these figures relate to anchoring in the cervical vertebrae, which are considered highly problematic due to the lack of cancellous bone volume. In contrast to conventional approaches, this preferred example of the present invention achieves effective anchoring by using four non-collinear regions of engagement which pass through cortical bone (surfaces). This mode of anchoring is referred to herein as "quadru-cortical bone engagement". The four regions of engagement are illustrated by numbered lines in FIGS. 22A and 23A. In the case of FIGS. 22A-22C, posterior access cervical bone anchoring is shown, whereas in the case of FIGS. 23A-23C anterior approach cervical bone anchoring is shown. In both cases, the anchoring element may be the elongated element 10 inserted during drilling. Alternatively, the entire drill assembly may be withdrawn and a separate anchoring element inserted in the channel.

Figure 24:
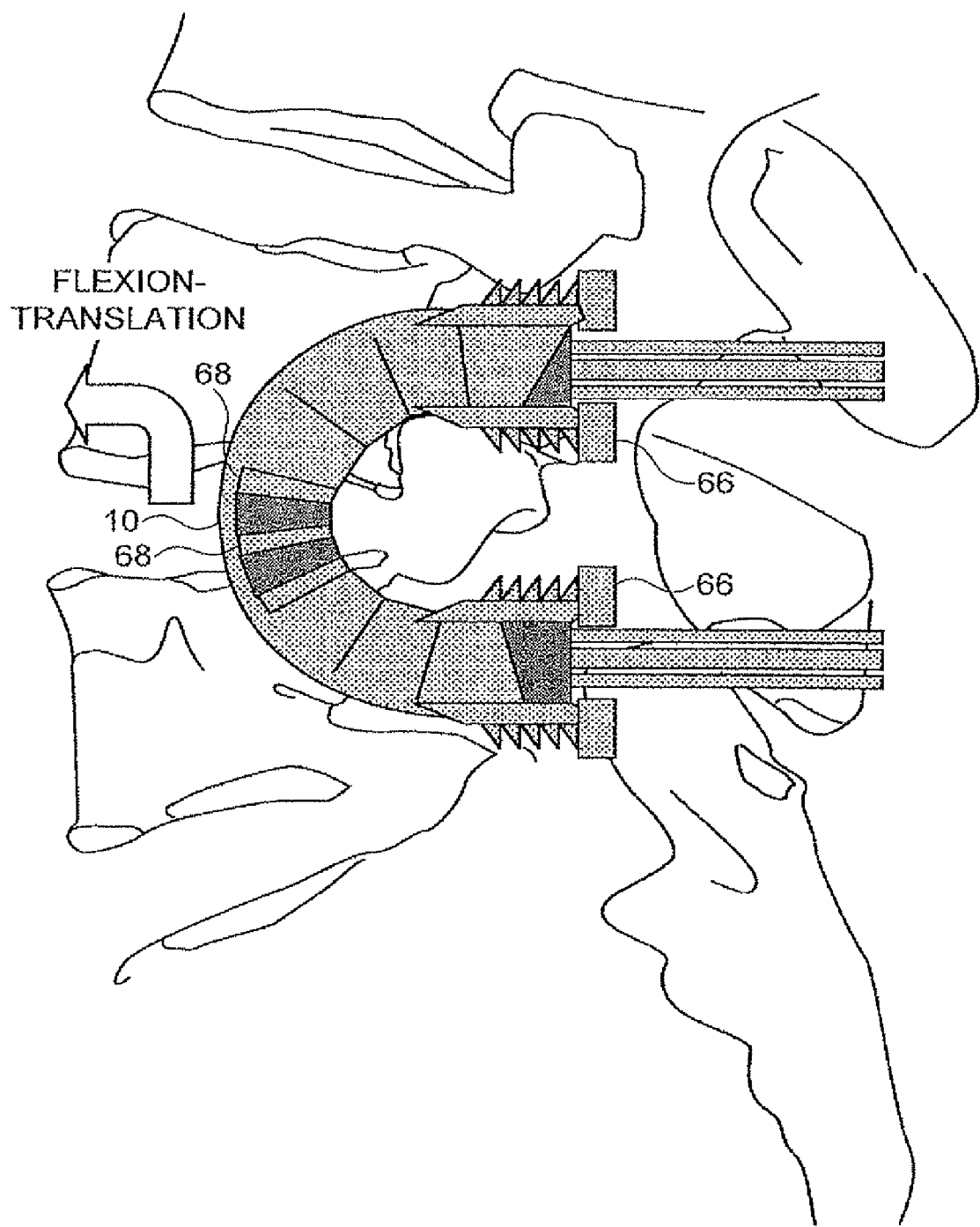
FIG. 24 is a schematic illustration of an implementation of the present invention for inter-vertebral disc reinforcement.

Turning now to FIG. 24, this illustrates a related technique and corresponding structure for inter-vertebral disc reinforcement. Specifically, there is shown an elongated element 10 according to the present invention passing vertically in a semicircular arc between pedicle screws 66 in vertically adjacent vertebrae. The properties of elongated element 10, and specifically the capability of opening up toward a lower-curvature state, allow significant relative movement between vertebrae for flexion or translation. At the same time, the opposition of the element against bending tighter than its predefined curved form provides significant vertical load-bearing ability, thereby maintaining spacing between the vertebrae and relieving pressure from the inter-vertebral disc (not shown). Optionally, additional resilient material 68 may be incorporated into elongated element 10 so as to provide an additional cushioning effect.

Figure 25B:
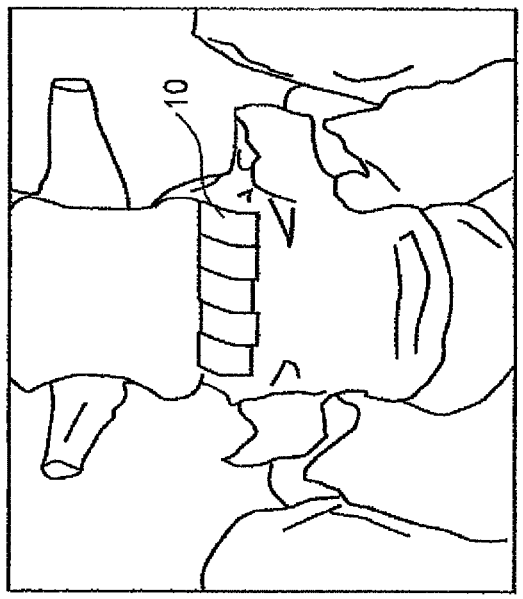
FIGS. 25A-25C are schematic lateral, anterior and axial views, respectively, showing an implementation of the present invention for inter-vertebral disc replacement.
Figure 25C:
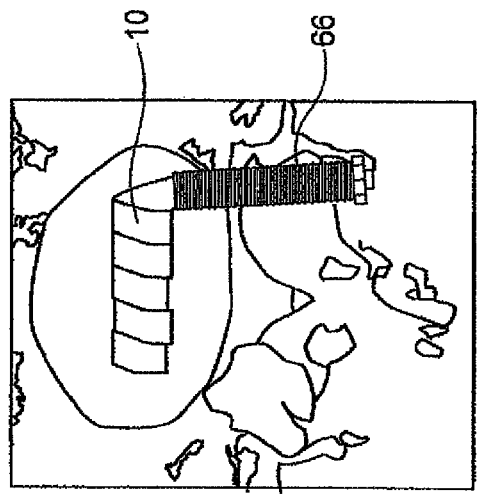
Figure 25A:
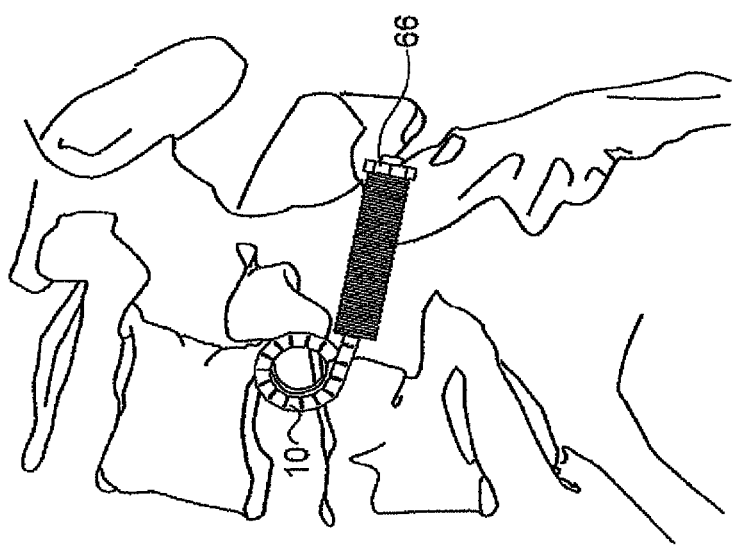

Turning now to FIGS. 25A-25C, these illustrate an application of a helical elongated element of the present invention as an inter-vertebral disc replacement. In this case, the element 10 is preferably inserted via a single pedicle screw 66 to which it is fixated after insertion. The external footprint of the helical implant is approximately cylindrical, and is positioned with its axis directed laterally, thereby providing support between adjacent vertebrae while allowing flexion motion.

Figure 26A:
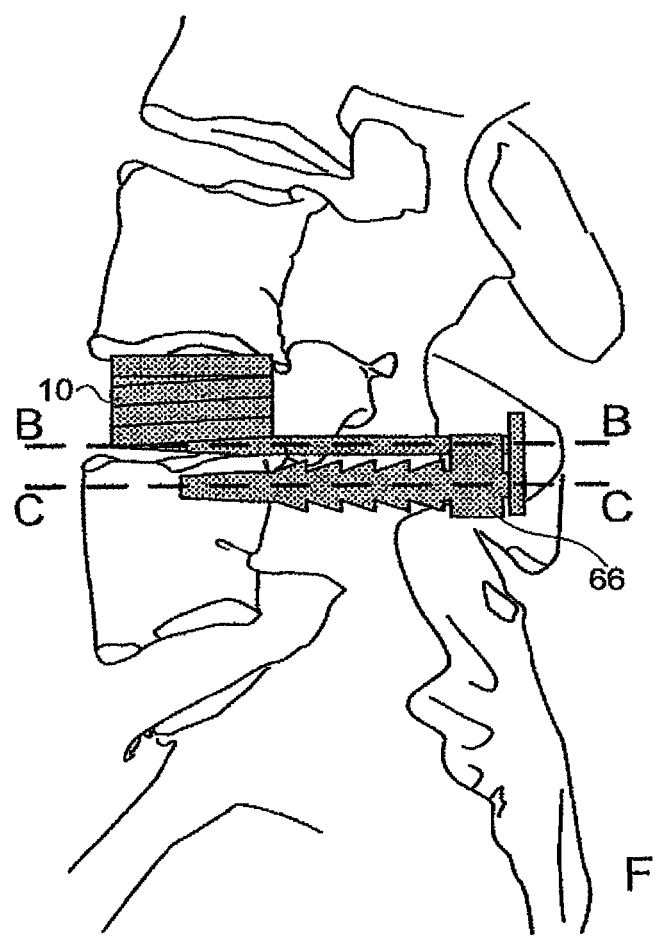
FIG. 26A is a schematic lateral view showing an implementation of the present invention for inter-vertebral disc replacement with adjustable height restoration.
Figure 26B:
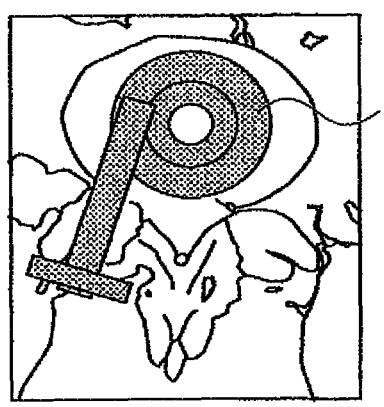
FIGS. 26B and 26C are axial cross-sectional views taken along lines B-B and C-C, respectively, in FIG. 26A.
Figure 26C:
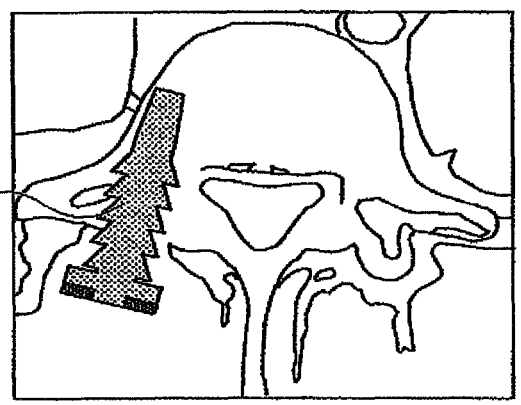

Turning now to FIGS. 26A-26C, these illustrate a further preferred implementation of the present invention employing the structure of FIG. 14 for inter-vertebral disc replacement with adjustable height restoration. In this case, the device is introduced directly between the pedicles into the inter-vertebral volume, preferably previously evacuated by a discectomy. As the elongated element it is introduced, the distal part of the elongated element first forms a flat spiral, thereby providing a non-abrasive contact surface for the upper (or lower) vertebra. Then, as the element is advanced further, the closed helix begins to accumulate, gradually lifting the upper vertebra away from the lower one until the desired height restoration is achieved. The elongated element is then anchored to a single pedicle screw 66 and severed to provide an anchored disc replacement.

Figure 27C:
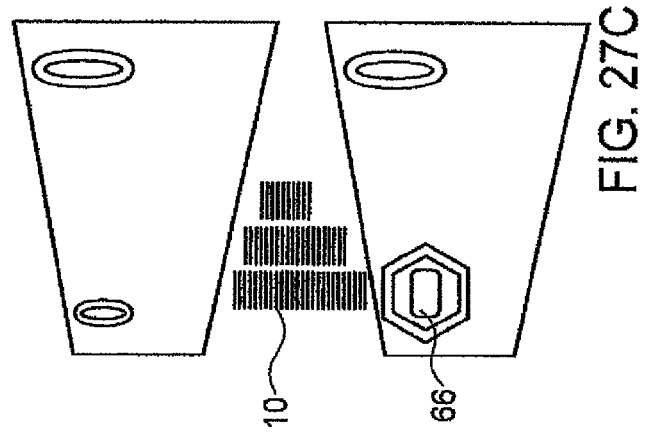
FIGS. 27A-27C are schematic posterior views of two adjacent vertebrae during progressive correction of scoliosis as a minimally invasive procedure according to the present invention.
Figure 27B:
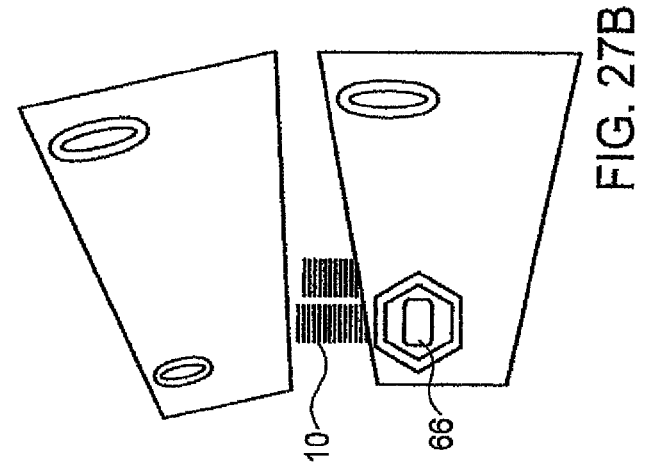
Figure 27A:
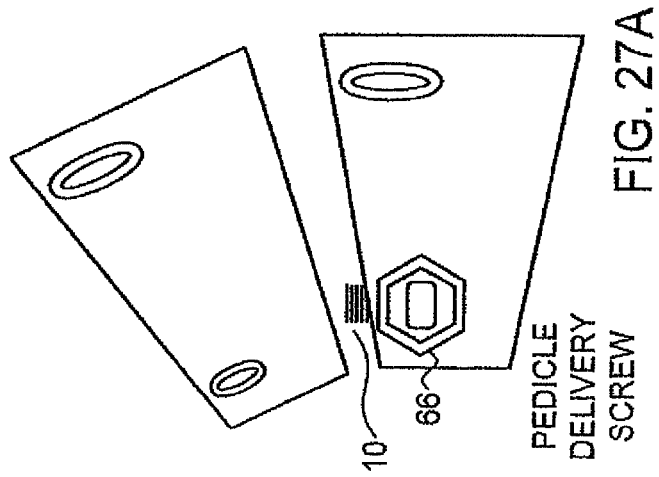

Turning now to FIGS. 27A-27C, these show schematically a minimally invasive procedure according to the present invention for progressive correction of scoliosis. In the implementation illustrated here, a spiral implementation of an elongated element is introduced through a pedicle delivery screw on the side of the spinal column where vertebral separation is required. As successive coils of the spiral form, the increasing diameter of the structure progressively lifts the side of the upper vertebra away from the lower vertebra. This process can be performed in parallel for a number of vertebrae. If the procedure is performed using only local anesthetic, the patient can be asked to stand between adjustments of the vertebral correction, and the adjustments can be performed iteratively until optimal correction is achieved. Here too, once the required correction has been achieved, the elements are fixated to the pedicle screw and severed, remaining as implants.

Figure 28C:
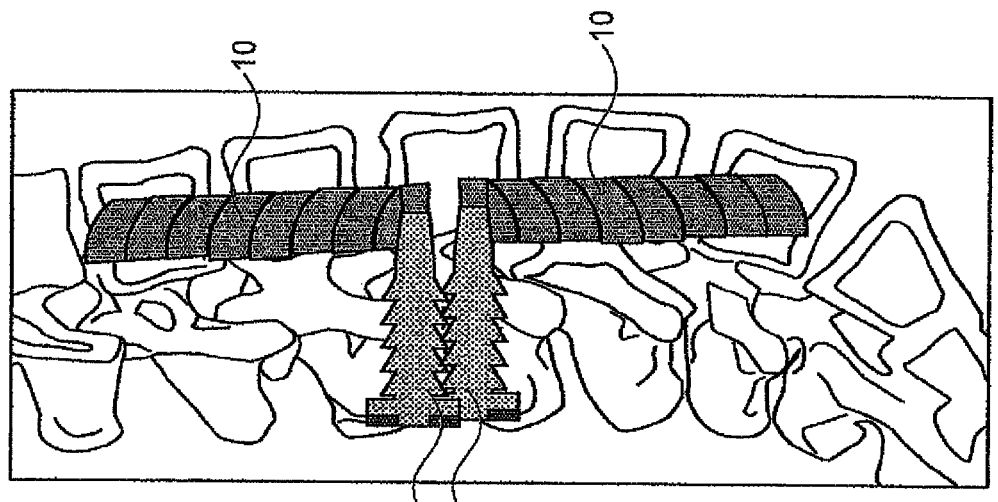
FIGS. 28A-28C are schematic sagittal cross-sectional views illustrating three variant implementations of multiple-segment vertebral body reinforcement according to the present invention.
Figure 28B:
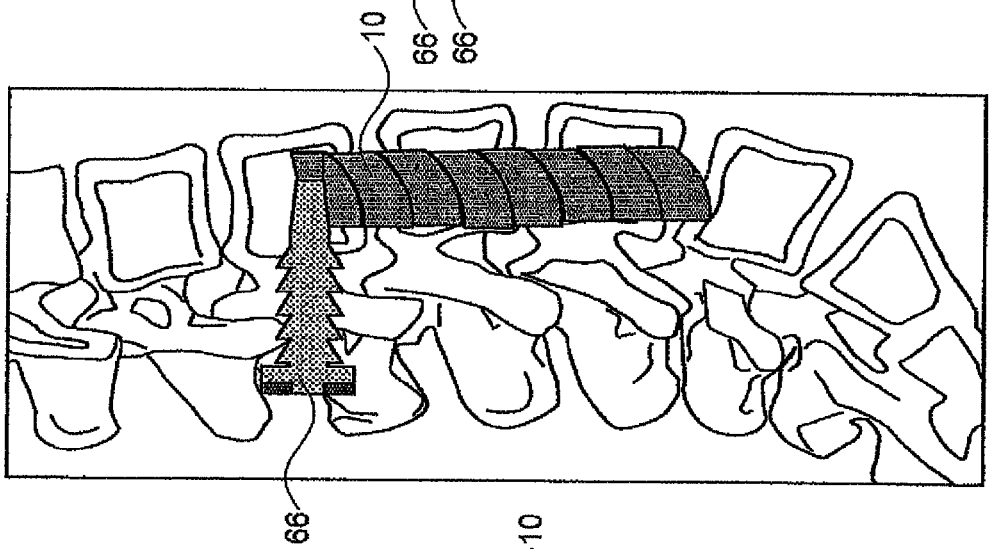
Figure 28A:
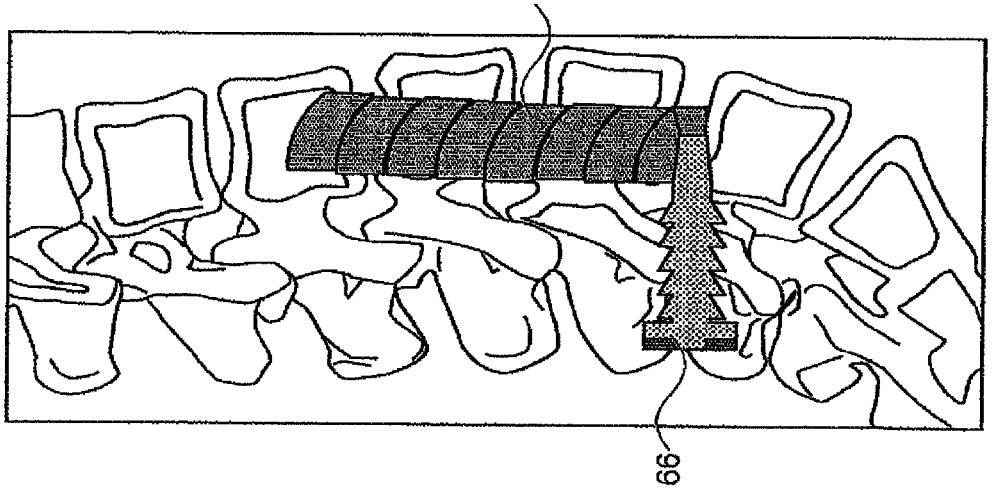

Turning now to FIGS. 28A-28C, these illustrate the use of elongated helical implementations of the present invention as multiple-segment vertebral body reinforcements. Specifically, by employing an elongated element 10 with a tight helical form, it is possible to introduce a reinforcing element via a single pedicle screw which will then extend vertically through the vertebral bodies and discs of multiple adjacent vertebrae. This provides reinforcement and support for the spinal column while preserving flexibility. The element may extend upwards as shown in FIG. 28A or downwards as shown in FIG. 28B. Since only one pedicle is needed for introduction of each element, it is further possible to introduce one element via a first pedicle extending upwards and second via the other pedicle extending downwards, as illustrated in FIG. 28C.

Figures 29A, 29B, 29C:
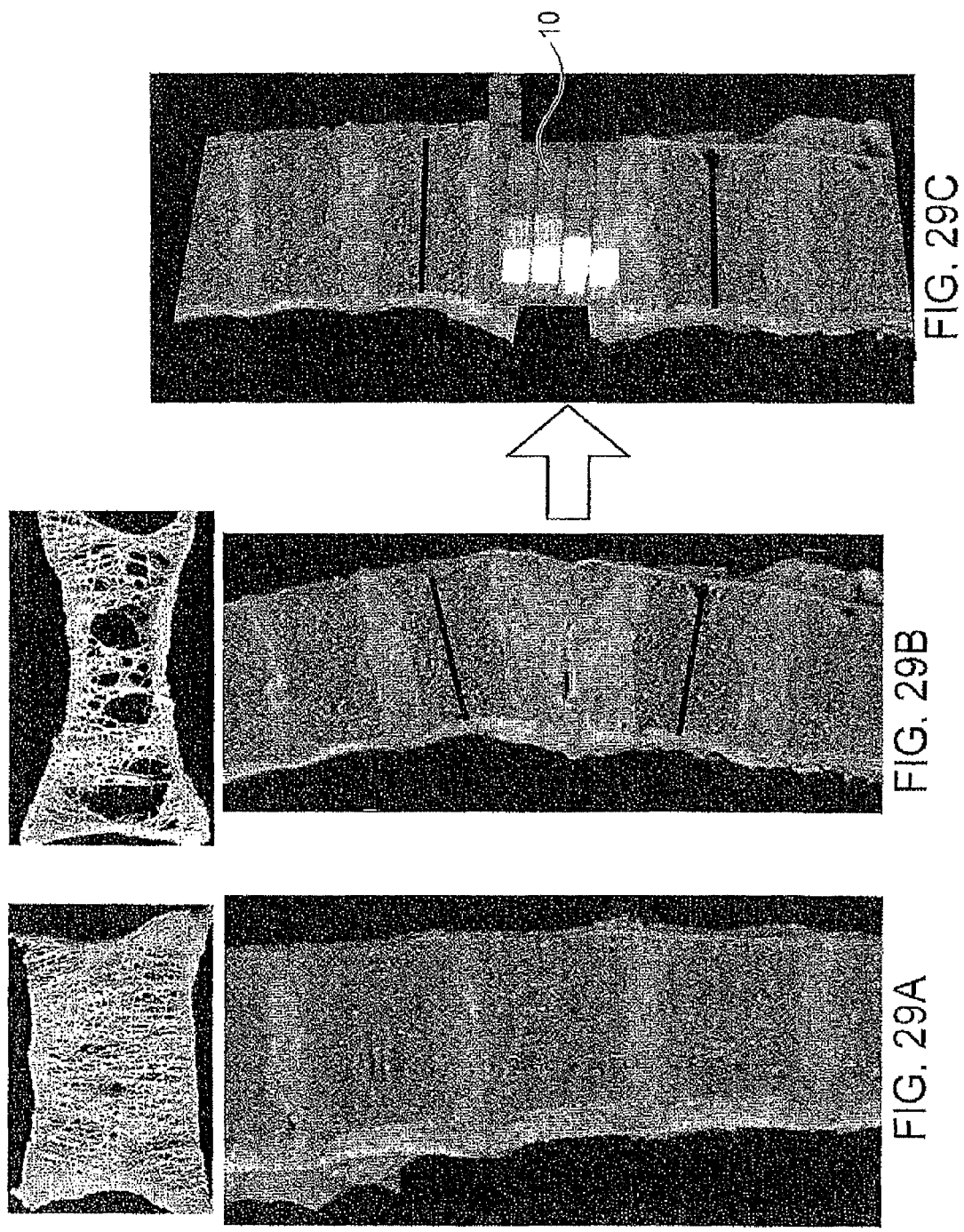
FIG. 29A is a sagittal cross-sectional view illustrating a spinal column with healthy vertebrae.
FIG. 29B is a view similar to FIG. 29A illustrating a collapsed vertebra.
FIG. 29C is a view of the spinal column of FIG. 29B illustrating schematically the restoration of vertebral height according to the teachings of the present invention.

Turning now to FIGS. 29A-29C, an implementation of the present invention for vertebral height restoration will now be described. Like in the height restoration for an intervertebral disc described above with reference to FIGS. 26A-26C, this aspect of the present invention is also advantageously implemented using the form of elongated element described above with reference to FIG. 14, and in a manner analogous to that described in FIGS. 26A-26C.

FIGS. 29A and 29B contrast a spinal column with healthy vertebrae against another with a collapsed vertebra. FIG. 29C illustrates the spinal column of FIG. 29B after introduction of an elongated element 10 according to the teachings of the present invention. The black lines overlaid over the vertebrae adjacent to the collapsed vertebra of FIGS. 29B and 29C show clearly the vertebral height restoration achieved. Optionally, the internal volume within the deployed element may be filled with suitable biocompatible material to impart additional structural or therapeutic properties. Examples of structural filling materials include, but are not limited to, bone cement, flexible biocompatible fillers and osteo-inductive agents for promoting bone growth, including bone grafts and bone marrow. Examples of therapeutic materials which can be introduced into the internal volume include, but are not limited to, antibiotics, anti-neoplastic agents and anti-mitotic agents.

Although only a very limited set of examples of applications of the present invention have been presented, it will be clear that it may be used in numerous other procedures and treatments in the medical field, as well as in other fields. For example, the various hollow implementations of the elongated element may optionally be used for sampling tissue, such as for a biopsy, or for removing tissue, such as for a discectomy.

It will be appreciated that the above descriptions are intended only to serve as examples, and that many other embodiments are possible within the scope of the present invention as defined in the appended claims.

What is claimed is:

1. A method for deploying an implant within a body, the method comprising the steps of:
    (a) deploying a conduit to define a first part of a path of insertion for an implant into the body;
    (b) advancing an implant along the conduit while the implant is in a straightened state; and
    (c) deploying the implant from the conduit so as to assume a curved state deployed laterally relative to a direction of elongation of the conduit,
    wherein the conduit has a generally rectangular transverse cross-section, at least part of said rectangular cross-section abutting part of the implant during said advancing such that, at the end of deployment of the implant, an orientation of the conduit defines an orientation of a proximal portion of the implant, and thereby defines an orientation of the laterally deployed implant relative to the conduit.

2. The method of claim 1, wherein a transverse cross-section of the implant has a substantially rectangular outer shape.

3. A method for deploying an implant within a body, the method comprising the steps of:
    (a) deploying a guide to define a first part of a path of insertion for an implant into the body;
    (b) advancing an implant along the guide while the implant is in a straightened state; and
    (c) deploying the implant from the guide so as to assume a curved state deployed laterally relative to a direction of elongation of the guide,
    wherein the guide has at least two substantially parallel surfaces, said parallel surfaces abutting the implant during said advancing such that, at the end of deployment of the implant, an orientation of the guide defines an orientation of a proximal portion of the implant, and thereby defines an orientation of the laterally deployed implant relative to the guide.

4. The method of claim 3, wherein the guide is a substantially rectangular conduit.

5. The method of claim 3, wherein a transverse cross-section of the implant has a substantially rectangular outer shape.

6. A system comprising:
    (a) a guide formed with at least two substantially parallel walls; and
    (b) an implant for insertion along said guide, said implant comprising at least two interconnected segments, said segments being deflectable from a straightened state to a deflected state in which said implant has a curved form, wherein said implant is temporarily limited to said straightened state during delivery along the guide, said implant being deflected laterally relative to a longitudinal direction of said guide and assuming said deflected state on leaving said guide, wherein, at the end of deployment of the implant, abutment of said substantially parallel walls against said implant defines an orientation of a proximal portion of the implant, and thereby defines an orientation of the laterally deployed implant relative to the guide.

7. The system of claim 6, wherein said guide is a rectangular conduit.

* * * * *